(12) United States Patent
Hefez et al.

(10) Patent No.: US 12,137,870 B2
(45) Date of Patent: *Nov. 12, 2024

(54) SYSTEMS AND METHODS FOR THROAT IMAGING

(71) Applicant: TYTO CARE LTD., Netanya (IL)

(72) Inventors: Josef Hefez, Tel-Aviv (IL); Eitan Sharif, Kibbutz Gesher Haziv (IL); Eyal Bychkov, Hod Hasharon (IL); David Gilad-Gilor, Even Yehuda (IL)

(73) Assignee: TYTO CARE LTD., Netanya (IL)

( * ) Notice: Subject to any disclaimer, the term of this patent is extended or adjusted under 35 U.S.C. 154(b) by 47 days.

This patent is subject to a terminal disclaimer.

(21) Appl. No.: 17/472,766

(22) Filed: Sep. 13, 2021

(65) Prior Publication Data

US 2021/0401273 A1 Dec. 30, 2021

Related U.S. Application Data

(63) Continuation of application No. 15/574,922, filed as application No. PCT/IL2016/050494 on May 10, 2016, now Pat. No. 11,141,047.

(Continued)

(51) Int. Cl.
*A61B 1/24* (2006.01)
*A61B 1/00* (2006.01)
(Continued)

(52) U.S. Cl.
CPC .. *A61B 1/000094* (2022.02); *A61B 1/000096* (2022.02); *A61B 1/00052* (2013.01);
(Continued)

(58) Field of Classification Search
CPC ........ A61B 1/24; A61B 1/247; A61B 1/00128
See application file for complete search history.

(56) References Cited

U.S. PATENT DOCUMENTS 6,257,238 B1 7/2001 Meah
6,554,765 B1 4/2003 Yarush et al.
(Continued)

FOREIGN PATENT DOCUMENTS

CN 1654011 A 8/2005
CN 103325128 A 9/2013
(Continued)

*Primary Examiner* — Anu Ramana
(74) *Attorney, Agent, or Firm* — S.J. Intellectual Property LTD.

(57) ABSTRACT

A portable handheld system for imaging of a throat of a patient, including: a mouthpiece including at least one bite guide for stabilizing the mouthpiece with respect to teeth of the patient when the patient bites on the at least one bite guide; intraoral optics operable to collect light from the throat of the patient and to direct the light towards an imaging sensor; and an imaging sensor operable to capture light directed by the intraoral optics to provide an image of the throat; wherein a mechanical connection between the mouthpiece and the intraoral optics constrains a spatial relationship of the intraoral optics with respect to the mouthpiece so that when the patient bites on the at least one bite guide: the intraoral optics is stabilized by the mouthpiece inside a mouth of the patient having a FOV which includes at least part of a tonsil of the patient.

15 Claims, 16 Drawing Sheets

Related U.S. Application Data

(60) Provisional application No. 62/163,468, filed on May 19, 2015.

(51) Int. Cl.
*A61B 1/247* (2006.01)
*A61B 5/00* (2006.01)
*G16H 40/63* (2018.01)
*G16Z 99/00* (2019.01)

(52) U.S. Cl.
CPC ...... *A61B 1/00128* (2013.01); *A61B 1/00148* (2022.02); *A61B 1/24* (2013.01); *A61B 1/247* (2013.01); *A61B 5/0088* (2013.01); *A61B 5/682* (2013.01); *G16H 40/63* (2018.01); *G16Z 99/00* (2019.02); *A61B 1/00135* (2013.01); *A61B 1/00142* (2013.01)

(56) References Cited

U.S. PATENT DOCUMENTS

| | | | |
|---|---|---|---|
| 7,494,338 B2* | 2/2009 | Durbin | A61C 9/00 433/29 |
| 2003/0148243 A1* | 8/2003 | Kerschbaumer | A61B 1/00052 433/29 |
| 2012/0088971 A1 | 4/2012 | Napier | |
| 2012/0288819 A1 | 11/2012 | Burrell et al. | |
| 2013/0209954 A1 | 8/2013 | Prakash et al. | |
| 2015/0087926 A1 | 3/2015 | Raz et al. | |
| 2016/0338804 A1* | 11/2016 | Kim | A61C 9/0006 |

FOREIGN PATENT DOCUMENTS

| | | |
|---|---|---|
| CN | 103370001 A | 10/2013 |
| EP | 2074951 A2 | 7/2009 |
| WO | 997015144 A1 | 4/1997 |
| WO | 2014110548 A1 | 7/2014 |
| WO | 2014117954 | 8/2014 |

\* cited by examiner

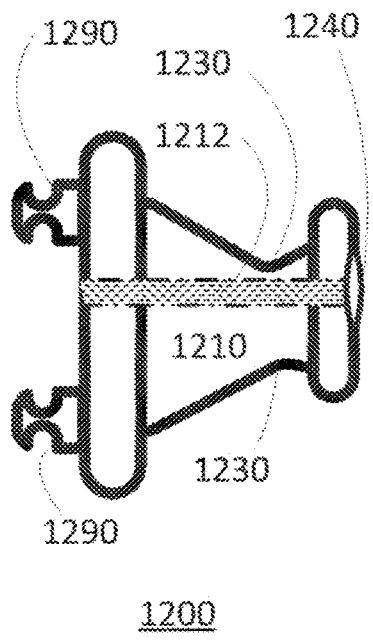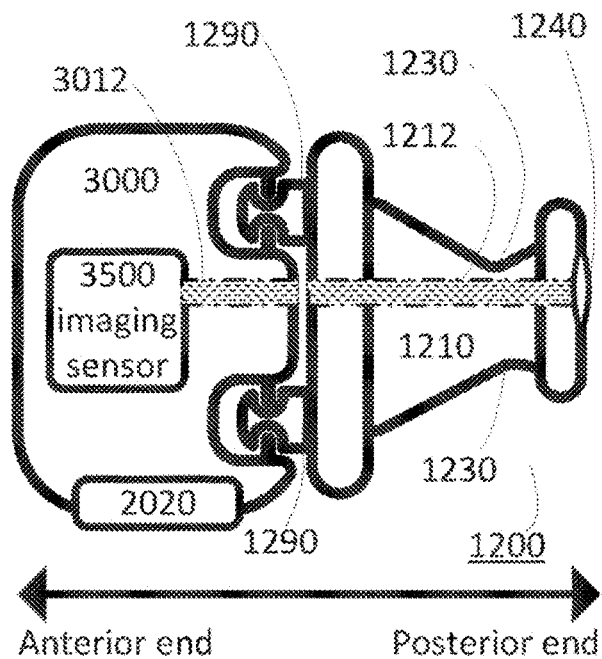
FIG. 12A  FIG. 12B
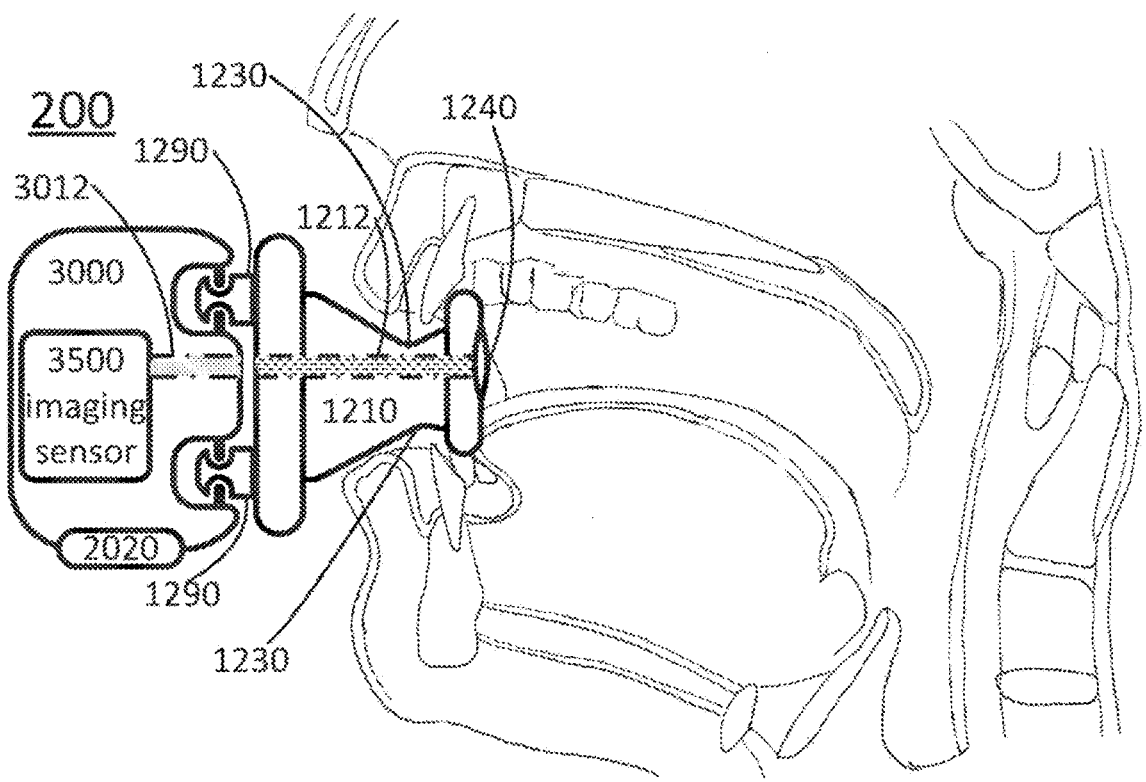
FIG. 12C

510
Stabilizing intraoral optics with respect to a mouth of the patient by a mouthpiece which is connected to the intraoral optics and which is stabilized with respect to the mouth by teeth of the patient which bite on at least one bite guide

520
During the stabilizing of stage 510, capturing light directed by the intraoral optics,to provide an image of the throat which include at least part of a tonsil of the patient

520
During the stabilizing of stage 510, capturing light directed by the intraoral optics, to provide an image of the throat which include at least part of a tonsil of the patient

521
capturing the image when a tongue of the patient is not mechanically forced down

FIG. 18

510
Stabilizing intraoral optics with respect to a mouth of the patient by a mouthpiece which is connected to the intraoral optics and which is stabilized with respect to the mouth by teeth of the patient which bite on at least one bite guide

511 constraining a spatial relationship of the intraoral optics with respect to the mouthpiece so that when the patient bites on the at least one bite guide: the intraoral optics is stabilized by the mouthpiece inside a mouth of the patient having a field of view which includes at least part of a tonsil of the patient

512 stabilizing with respect to the mouth of the patient an imaging sensor which is mechanically connected to the mouthpiece and which executes the capturing of the image

513 stabilizing the intraoral optics within the oral cavity proper of the patient

514 stabilizing a posteriormost optical component of the intraoral optics posterosuperiorly to an inferiormost point of any maxillary central incisor of the patient

FIG. 17

610
Inserting partly into a mouth of the patient a mouthpiece of a portable handheld system which includes an imaging sensor which is mechanically connected to the mouthpiece, the inserting including inserting into the mouth intraoral optics that are mechanically connected to the mouthpiece.

620
Biting by the patient on at least one bite guide of the mouthpiece, for stabilizing the mouthpiece with respect to the mouth, thereby stabilizing the intraoral optics within the mouth having a field of view which includes at least part of a tonsil of the patient

630
Resuming the stabilizing at least until the imaging sensor captures an image of the throat of the patient which includes at least part of a tonsil of the patient.

640 receiving from a medical expert a result of a diagnosis by the medical expert which is based on the image

650 receiving from a medical expert a medical recommendation for treating a medical condition of the patient, identified by the medical expert based on the image

FIG. 20

ND METHODS FOR THROAT IMAGING

SYSTEMS AND METHODS FOR THROAT IMAGING

RELATED APPLICATIONS

This application claims priority from U.S. provisional patent application Ser. No. 62/163,468, filing date May 19, 2015.

FIELD

The invention related to systems and methods for throat imaging, and especially to systems and methods for imaging tonsils.

BACKGROUND

Visual inspection of the throat, and especially of the tonsils, provides data indicative of various physiological conditions such as sore throat, tonsillitis (an infection in the tonsils), pharyngitis (inflammation of the pharynx), strep throat, mononucleosis, gastric reflux.

Such visual inspection is traditionally performed manually by physicians, and may also be performed using specialized equipment (especially cameras) by trained personnel, which was specifically trained in order how to obtain images of the throat of sufficient quality, using the specialized equipment. Some forms of visual inspection deeper down the throat (such as laryngoscopy) may even require anesthetization in addition to expert operation of the laryngoscope.

Further limitations and disadvantages of conventional, traditional, and proposed approaches will become apparent to one of skill in the art, through comparison of such approaches with the subject matter of the present application as set forth in the remainder of the present application with reference to the drawings.

GENERAL DESCRIPTION

According to an aspect of the invention, a system for imaging of a throat of a patient is disclosed, the system including: (a) a mouthpiece including at least one bite guide for stabilizing the mouthpiece with respect to teeth of the patient when the patient bites on the at least one bite guide; (b) intraoral optics operable to collect light from the throat of the patient and to direct the light towards an imaging sensor, the intraoral optics being mechanically coupled to the mouthpiece; and (c) an imaging sensor operable to capture light directed by the intraoral optics to provide an image of the throat; wherein the mechanical connection between the mouthpiece and the intraoral optics constrains a spatial relationship of the intraoral optics with respect to the mouthpiece so that when the patient bites on the at least one bite guide: the intraoral optics is stabilized by the mouthpiece inside a mouth of the patient having a field of view which includes at least part of a tonsil of the patient; wherein the system is a portable handheld system According to a further aspect of the invention, a system is disclosed wherein the spatial relationship of the intraoral optics with respect to the mouthpiece as constrained by the mechanical connection, enables the imaging sensor to image the at least part of the tonsil when a tongue of the patient is not mechanically forced down.

According to a further aspect of the invention, a system is disclosed further including a tongue depressor mechanically connected to the mouthpiece so as to enable the tongue depressor to depress a tongue of the patient when the patient bites on the at least one bite guide.

According to a further aspect of the invention, a system is disclosed wherein the imaging sensor is mechanically connected to mouthpiece so as to constrain a spatial relationship in which the imaging sensor is located in the oral cavity proper of the patient during the capturing of the image.

According to a further aspect of the invention, a system is disclosed wherein the mechanical connection between the mouthpiece and the intraoral optics constrains a spatial relationship of the intraoral optics with respect to the at least one bite guide such that the intraoral optics are located in the oral cavity proper of the patient when the patient bites on the at least one bite guide.

According to a further aspect of the invention, a system is disclosed wherein the imaging sensor is operable to capture the image when a posteriormost optical component of the intraoral optics is located posterosuperiorly to an inferiormost point of any maxillary central incisor of the patient.

According to a further aspect of the invention, a system is disclosed further including a handgrip for gripping the system by the patient, for carrying the system by the patient to a position in which the patient can bite on the at least one bite guide.

According to a further aspect of the invention, a system is disclosed further including a user interface operable to indicate to the patient when a location of the mouthpiece enables capturing of the image by the imaging sensor.

According to a further aspect of the invention, a system is disclosed wherein the mouthpiece includes an opening through which passes a traversing optical path from the intraoral optics to the imaging sensor, wherein the opening is located closer to a top part of the mouthpiece than to a bottom part of the mouthpiece.

According to a further aspect of the invention, a system is disclosed further including a processor configured and operable to trigger capturing of the image by the imaging sensor in response to information received from at least one detector of the system, wherein a distance between the processor and a posteriormost bite guide out of the at least one bite guide is smaller than 10 centimeters.

According to a further aspect of the invention, a system is disclosed further including a processor configured and operable to trigger capturing of the image by the imaging sensor based on determining that a tongue of the patient is extended outside a mouth of the patient and touches an extraoral part of the system.

According to a further aspect of the invention, a system is disclosed, further including a display which is mechanically connected to the mouthpiece, the display being operable to display images concurrently to the capturing of the image by the imaging sensor.

According to a further aspect of the invention, a system is disclosed, further including a display, operable to display instructions indicative of a required change in a state of the system, for enabling acquisition of the image.

According to a further aspect of the invention, a system is disclosed, wherein the processor is configured and operable to provide to an external system image data obtained by the imaging sensor, for displaying on a monitor of the external system.

According to a further aspect of the invention, a system is disclosed, including a casing including the imaging sensor, the casing including a mechanical fastener for connection of specula used for investigating body orifices; wherein the mouthpiece separable from the casing, and includes a at least one fastener for mechanically detachably fastening mouthpiece to the mechanical fastener of the casing; wherein the system includes at least one speculum for examination of a body orifice selected from the group consisting of: ear, nostril, rectum, and vagina; wherein the imaging sensor is further operable to capture an image of the body orifice when the speculum is at least partly inserted into a respective body orifice of the patient.

According to an aspect of the invention, a bitable camera stabilization system is disclosed, the bitable camera stabilization system including: (a) a bitable support including a at least one bite guide for stabilizing the bitable support with respect to teeth of the patient when the patient bites on the at least one bite guide; (b) intraoral optics operable to collect light from the throat of the patient and to direct the light towards an internal optical path intrinsic to the bitable support, the intraoral optics being mechanically connected to the bitable support; wherein the mechanical connection between the bitable support and the intraoral optics constrains a spatial relationship of the intraoral optics with respect to the bitable support so that when the patient bites on the at least one bite guide: the intraoral optics is stabilized by the bitable support inside a mouth of the patient having a field of view which includes at least part of a tonsil of the patient; (c) at least one fastener for mechanically detachably fastening the bitable support to an external portable handheld camera which includes an imaging sensor, so as to create an optical path between the intraoral optics and the imaging sensor, the optical path including the internal optical path and an external optical path passing within the portable handheld camera.

According to a further aspect of the invention, a bitable camera stabilization system is disclosed, wherein the at least one fastener is operable to mechanically detachably fasten the bitable support to the external portable handheld camera for stabilizing the imaging sensor with respect to the at least one bite guide, so that when the patient bites on the at least one bite guide, the imaging sensor is stable with respect to a throat of the patient.

According to a further aspect of the invention, a bitable camera stabilization system is disclosed, wherein the spatial relationship of the intraoral optics with respect to the bitable support constrained by the mechanical connection, enables the intraoral optics to collecting light arriving from at least part of the tonsil when a tongue of the patient is not mechanically forced down.

According to a further aspect of the invention, a bitable camera stabilization system is disclosed, further including a tongue depressor mechanically connected to the bitable support so as to enable the tongue depressor to depress a tongue of the patient when the patient bites on the at least one bite guide.

According to a further aspect of the invention, a bitable camera stabilization system is disclosed, wherein the mechanical connection between the bitable support and the intraoral optics constrains a spatial relationship of the intraoral optics with respect to the at least one bite guide such that the intraoral optics are located in the oral cavity proper of the patient when the patient bites on the at least one bite guide.

According to a further aspect of the invention, a bitable camera stabilization system is disclosed, wherein the mechanical connection between the bitable support and the intraoral optics constrains a spatial relationship of the intraoral optics with respect to the at least one bite guide such that a posteriormost optical component of the intraoral optics is located posterosuperiorly to an inferiormost point of any maxillary central incisor of the patient when the patient bites on the at least one bite guide.

According to a further aspect of the invention, a bitable camera stabilization system is disclosed, further including a handgrip connected to the bitable support for carrying the system by the patient to a position in which the patient can bite on the at least one bite guide.

According to a further aspect of the invention, a bitable camera stabilization system is disclosed, wherein an opening of the internal optical path is located closer to a top part of the bitable support than to a bottom part of the bitable support.

According to an aspect of the invention, a method for imaging of a throat of a patient is disclosed, the method including: (a) stabilizing intraoral optics with respect to a mouth of the patient, by a mouthpiece which is connected to the intraoral optics and which is stabilized with respect to the mouth by teeth of the patient which bite on at least one bite guide; and (b) during the stabilizing, capturing light directed by the intraoral optics, to provide an image of the throat which include at least part of a tonsil of the patient; wherein the intraoral optics and the mouthpiece are parts of a portable handheld system.

According to a further aspect of the invention, a method is disclosed, wherein the stabilizing includes constraining a spatial relationship of the intraoral optics with respect to the mouthpiece so that when the patient bites on the at least one bite guide: the intraoral optics is stabilized by the mouthpiece inside a mouth of the patient having a field of view which includes at least part of a tonsil of the patient.

According to a further aspect of the invention, a method is disclosed, wherein the stabilizing further includes stabilizing with respect to the mouth of the patient an imaging sensor which is mechanically connected to the mouthpiece and which executes the capturing of the image.

According to a further aspect of the invention, a method is disclosed, wherein the capturing includes capturing the image when a tongue of the patient is not mechanically forced down.

According to a further aspect of the invention, a method is disclosed, further including depressing a tongue of the patient concurrently to the capturing.

According to a further aspect of the invention, a method is disclosed, wherein the stabilizing includes stabilizing the intraoral optics within the oral cavity proper of the patient.

According to a further aspect of the invention, a method is disclosed, wherein the stabilizing includes stabilizing a posteriormost optical component of the intraoral optics posterosuperiorly to an inferiormost point of any maxillary central incisor of the patient.

According to a further aspect of the invention, a method is disclosed, further including indicating to the patient when a location of the mouthpiece enables capturing of the image.

According to a further aspect of the invention, a method is disclosed, including displaying images concurrently to the capturing by a display whose distance from a posteriormost bite guide out of the at least one bite guide is smaller than 10 centimeters.

According to a further aspect of the invention, a method is disclosed, further including displaying instructions indicative of a change in a state of the system which is required for enabling acquisition of the image.

According to a further aspect of the invention, a method is disclosed, further including providing to an external system image data of the throat of the patient, for displaying on a monitor of the external system.

According to an aspect of the invention, a method for imaging of a throat of a patient is disclosed, the method including: (a) inserting partly into a mouth of the patient a mouthpiece of a portable handheld system which includes an imaging sensor which is mechanically connected to the mouthpiece, the inserting including inserting into the mouth intraoral optics that are mechanically connected to the mouthpiece; (b) biting by the patient on at least one bite guide of the mouthpiece for stabilizing the mouthpiece with respect to the mouth, thereby stabilizing the intraoral optics within the mouth having a field of view which includes at least part of a tonsil of the patient; and (c) resuming the stabilizing at least until the imaging sensor captures an image of the throat of the patient which includes at least part of a tonsil of the patient.

According to a further aspect of the invention, a method is disclosed, wherein the inserting is executed by the patient.

According to a further aspect of the invention, a method is disclosed, further including uttering a voice at least partly concurrently to the resuming, thereby lowering a tongue of the patient within the mouth for exposing the at least part of the tonsil to the intraoral optics.

According to a further aspect of the invention, a method is disclosed, wherein the inserting includes gripping a handgrip of the portable handheld system by the patient and moving the portable handheld system by the patient by moving the handgrip.

According to a further aspect of the invention, a method is disclosed, wherein the inserting is executed by the patient in response to indications by the portable handheld system indicating when a location of the mouthpiece enables capturing of the image.

According to a further aspect of the invention, a method is disclosed, wherein the inserting is executed by the patient in response to instructions by the portable handheld system indicating a change in a state of the system which is required for acquisition of the image.

According to a further aspect of the invention, a method is disclosed, wherein the inserting is executed by the patient in response to image data captured by the imaging sensor which is displayed on a monitor of an external system detached from the portable handheld system.

According to a further aspect of the invention, a method is disclosed, further including: detaching the mouthpiece from a casing of the portable handheld system which includes the imaging sensor; connection to the casing a speculum for examination of a body orifice selected from the group consisting of: ear, nostril, rectum, and vagina; and holding the portable handheld system when the speculum is at least partly inserted into a respective body orifice of the patient at least until the imaging sensor captures an image of the body orifice.

According to a further aspect of the invention, a method is disclosed, wherein the holding is followed by opening the mouth by the patient, so as to release a holding of the portable handheld system.

According to a further aspect of the invention, a method is disclosed, wherein the holding is followed by removing the portable handheld system from the mouth of the patient, after the patient opened the mouth for releasing the portable handheld system.

According to a further aspect of the invention, a method is disclosed, further including receiving from a medical expert a result of a diagnosis by the medical expert which is based on the image.

According to a further aspect of the invention, a method is disclosed, further including receiving from a medical expert a medical recommendation for treating a medical condition identified by the medical expert based on the image.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 12A is a functional block diagram illustrating an example of a bitable camera stabilization system, in accordance with examples of the presently disclosed subject matter;

FIG. 12B is a functional block diagram illustrating an example of a bitable camera stabilization system when connected to external portable handheld camera, in accordance with examples of the presently disclosed subject matter;

FIG. 12C is a functional block diagram illustrating an example of a bitable camera stabilization system, when connected to external portable handheld camera and when the patient bites on the bite guides of the system, in accordance with examples of the presently disclosed subject matter

FIG. 16 is a flow chart illustrating an example of a method for imaging of a throat of a patient, in accordance with examples of the presently disclosed subject matter;

FIGS. 17 and 18 illustrate optional sub-stages of stages of the method of FIG. 16, in accordance with examples of the presently disclosed subject matter;

FIG. 20 is a flow chart illustrating an example of method 600, in accordance with examples of the presently disclosed subject matter. Method 600 is a method for imaging of a throat of a patient.

Figure 1:
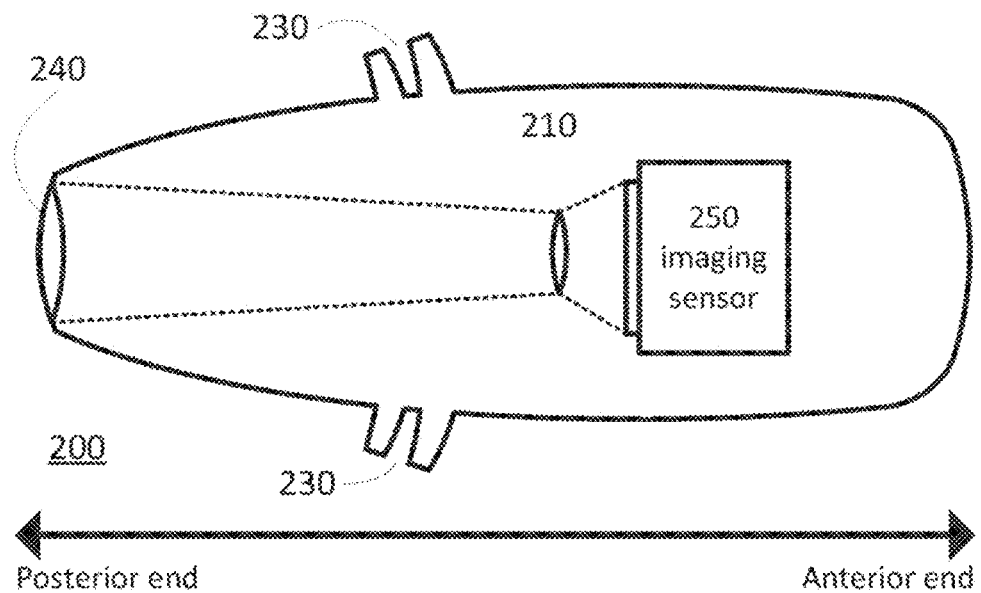
FIG. 1 is a functional block diagram illustrating an example of a system for imaging of a throat of a patient, in accordance with examples of the presently disclosed subject matter.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "processing", "determining", "generating", "selecting", or the like, include action and/or processes of a computer that manipulate and/or transform data into other data, said data represented as physical quantities, e.g. such as electronic quantities, and/or said data representing the physical objects. The terms "computer", "processor", and "controller" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

FIG. 1 is a functional block diagram illustrating an example of system 200, which is a system for imaging of a throat of a patient, in accordance with examples of the presently disclosed subject matter. As discussed below in greater detail, system 200 may be used by the patient herself for imaging her own throat (whether for her own use, or to be used by another person or system, such as a medical personal or a medical system). However, system 200 may also be used for imaging the throat of the patient by another person.

System 200 is a portable handheld system. That is, the physical dimensions of system 200, as well as its weight and the materials it is made of, enable a person to carry it on her person unassisted, and to operate it without any external mechanical support. System 200 is therefore sufficiently small and light to be operated while held in one or both hands (or in some cases, as will be demonstrated below, held by the teeth of the patient). Depending on its designated target audience, system 200 may be designed to be sufficiently small and light to be handled by an unassisted child.

System 200 includes imaging sensor 250, which may be for example a camera, a charge coupled device (CCD) array, and so on. System 200 further includes optics for directly light from the throat of the patient (and possibly also from the mouth or other intraoral parts of the patient). Such optics include intraoral optics 240 (represented in the illustrative example of FIG. 1 by a single lens) which are operable to collect light at least from the throat of the patient (and possibly also from other parts) and to direct the light towards imaging sensor 250, when intraoral optics 240 are located within a mouth of the patient. It is noted that the term "optics" refers to an array of one or more optical component. The optics (whether intraoral or extraoral) may include any known optical component, such as lenses, mirrors, prisms, optical filters, optical fibers, etc.).

In addition to directing of the light (e.g. by refraction, reflection, diffraction, etc.), intraoral optics (or other optics of system 200) may also be used to otherwise manipulate the light (e.g. by filtering it based on wavelength, amplitude, etc.). It is noted that the optics of system 200 may further include extraoral optics (not shown in FIG. 1), for further directing, refracting or otherwise manipulating of light before it reaches imaging sensor 250 (if the latter is located outside the mouth during image acquisition). Imaging sensor 250 is operable to capture light directed by intraoral optics 240 (some or all of that light) to provide an image of the throat.

Intraoral optics 240 are mechanically connected to mouthpiece 210, for supporting intraoral optics 240 by mouthpiece 210. Such a connection may be a rigid connection, a semirigid connection, and so on. Furthermore, other parts of system 200 may also be mechanically connected to mouthpiece 210 for support (e.g. extraoral optics if any, imaging sensor 250, a display if any, etc.). Such mechanical connections may be direct mechanical connection, or intermediated mechanical connection (via one or more connecting components such as washer, spacer, screw, bearing, fastener, etc.). Optionally, one or more of the mechanical connections between mouthpiece 210 and any other component of system 200 (e.g. optical components, imaging sensor 250, power source, etc.) may be attached detachably and reattachably (e.g. for connecting the imaging sensor of a multipurpose camera to mouthpiece 210, to serve as imaging sensor 250).

The mechanically coupling may be used to stabilize intraoral optics 240 (and possibly also imaging sensor 250 and intermediating optical components) and the imaged object (e.g. a selected portion of the pharynx) on the same mechanical axis.

Referring to mouthpiece 210, system 200 includes mouthpiece 210 which can be placed partly inside a mouth of the patient, and held by the patient using her teeth, possibly with additional holding of her lip or lips (but not necessarily so).

Mouthpiece 210 includes at least one bite guides 230 onto which the patient may bite when mouthpiece 210 is located partly inside her mouth, for securing mouthpiece 210. The at least one bite guides 230 are used for stabilizing mouthpiece 210 with respect to teeth of the patient when the patient bites on one or more of the at least one bite guides 230. The stabilization of the mouthpiece 210 results in stabilization of at least one other component of system 200 mechanically connected to mouthpiece 210 (e.g. some or all of intraoral optics 240 and/or imaging sensor 250), when the patient bites on the at least one bite guides 230. Based on the way mouthpiece 210 and the one or more bite guides 230 connected to it are usable for stabilization of system 200 (or at least few of its components) are stabilized with respect to the mouth of the patient, mouthpiece 210 may be regarded as a bitable mechanical support.

The concepts of stability and of stabilizing one object with respect to another are well accepted in the art. The term "stability" which is well accepted in the art, should be construed in a non-limiting way to include the quality or state of something that is not easily changed or moved, either by external forces or by internal forces. The term "stable" which is well accepted in the art, should be construed in a non-limiting way to include the quality or state of being relatively unchanging, and firmly fixed. The concept of "stabilizing a first object with respect to a second object" is well accepted in the art, and should be construed in a non-limiting way to include keeping the spatial relationship between the first object and the second object not easily changeable, and making it difficult to move the first object with respect to the second object, either by external forces or by forces internal to any one of the first and second objects.

The term "bite on an object" is well accepted in the art, should be construed in a non-limiting way to include applying force onto the object by one or more teeth. It is noted that while biting on an object may include applying the force by the teeth in the coronal direction (the direction towards the crown of a tooth, as opposed to apical, which refers to the direction towards the tip of the root), biting on an object may also include applying force by the teeth on the object in other directions, especially in the lingual direction (in the direction towards the tongue) or in the facial direction (from the side of the tooth which is adjacent to the inside of the cheek or of the lip, outwards towards the cheek or the lip).

It is noted that system 200 may include bite guide (or bite guides) 230 fitting for biting with maxillary teeth (i.e. teeth of the upper jaw, e.g. maxillary incisors, maxillary premolars, etc.), bite guide (or bite guides) 230 fitting for biting with mandibular teeth (i.e. teeth of the lower jaw, e.g. mandibular incisors, mandibular molars, etc.), or a combination of both.

The extent to which the patient needs to open her mouth for biting on system 200 may be determined based on various factors, such as lighting level, comfort, effect on positioning and/or visibility of different body organs, and so on. Optionally, system 200 may be designed in order to minimize the extent to which the mouth needs to open in order to allow operation of system 200. Optionally, the acquisition of the image by imaging sensor 250 is executed when the maxillary teeth and the mandibular teeth are less than 50% of their maximum opening. Optionally, the acquisition of the image by imaging sensor 250 is executed when a distance between the maxillary incisors and the mandibular incisors is less than 3 centimeters.

Referring to the at least one bite guide 230, it is noted that system 200 may include bite guides 230 matching to different subgroup of teeth (e.g. incisors only, incisors and canines, canines and premolars, etc.), depending on various factors such as necessary bite strength, locations of other components of system 200, and so on. It is noted that it is not necessary that all of the teeth of any of the jaws will touch the bite guides 230 for stabilization, and that stabilization may be achieved with a limited number of teeth.

It is noted that the shape of any one or more bite guide 230 (or the spatial relation between two or more bite guides 230) may optionally be adjustable by the patient (or by another person), to better fit a mouth of a specific patient. However, optionally a shape of mouthpiece 210 is unadjustable for fitting to the patient prior to the biting (a "one size fits all" implementation).

Furthermore, system 200 may include a plurality of superfluous bite guides 230, e.g. in order to match different mouth sizes, while stabilization may be achieved by biting of only few of them (e.g. biting into one upper bite guide 230 and one lower bite guide 230).

The stabilization of mouth piece 210 may be achieved by pressing of teeth of the patient against the bite guide 230. Counterforce for the biting of any of the teeth may be provided by biting with teeth of the opposite jaw, or with supporting with other parts of the mouth (e.g. gums, lips).

Optionally, system 200 may include a superior bite guide (conveniently denoted 231, for differentiation) and an inferior bite guide (conveniently denoted 232, for differentiation), where best stabilization is achieved when the patient bites onto both of these bite guides simultaneously, but this is not necessarily so.

It is noted that the one or more bite guides 230 may be implemented in a wide variety of forms, shapes, and materials, and therefore only few examples will be provided. By way of non-limiting examples only, the bite guides may take any one of the following forms:

a. One or more protrusions extending outwards of mouthpiece 210 (e.g. as exemplified in FIG. 1). Such one or more protrusions may have different shapes (e.g. circular, elongated, etc.), and each one of them may be designed to support one or more teeth of the patient. Such protrusions may be designed to be supported by anterior parts of the teeth, by posterior parts of the teeth, or both.

b. One or more depressions extending into mouthpiece 210, each such depression matching for one or more teeth of the patient.

c. A groove in mouthpiece 210 into which a plurality of teeth of the patient may be inserted for support (e.g. as exemplified in FIG. 2).

d. A soft material (e.g. rubber, other materials having hardness lower than 70 a shore.), into which the patient may bite, thereby depressing it into a shape which provides support to the teeth.

e. An external frame distanced from a body of mouthpiece 210 by at least one separator (e.g. washer).

It is noted that optionally, a biting guide 230 of system 200 may be ergonomically shape to follow a curve of a plurality of teeth out of a corresponding dental arch (e.g. the maxillary dental arch or the mandibular dental arch, corresponding to the teeth which the specific biting guide 230 is designed for). This is exemplified in FIG. 2. Matching a shape of biting guide to that of one or more tooth of a group of patients may be used for various reasons, such as in order to improve stability, to improve comfort of use, and so on.

It is noted that the shape and the materials of mouthpiece 210 and the one or more bite guides 230 allow partial insertion of mouthpiece 210 sufficiently into the mouth of the patient to enable acquisition of the throat (also referred to as "pharynx") of the patient, and especially of one or more of the tonsils (or parts of such tonsils).

Bite guide 230 and/or any other component of system 200 may be made from biocompatible material.

As mentioned above, mouthpiece 210 and intraoral optics 240 are mechanically connected to each other. The mechanical connection between mouthpiece 210 and intraoral optics 240 is such that constrains a spatial relationship of intraoral optics 240 with respect to mouthpiece 210 (thereby also, when bitten, to the teeth, and possibly to the mouth, pharynx, etc.) so that when the patient bites on the at least one bite guide 230, it results in that intraoral optics 240 is stabilized by mouthpiece 210 inside a mouth of the patient having a field of view which includes at least part of a tonsil of the patient.

The optics of the system (intraoral optics 240 and any further optical components on the optical path between intraoral optics 240 and imaging sensor 250, if any) are intended to collect light moving in a substantially posteroanterior direction, in the direction from the back of the throat towards the opening of the mouth. However, the optics of the system may be designed to collect such light having traverse (i.e. left/right) component and/or sagittal (i.e. up/down) component in addition to the posteroanterior component.

It is noted that imaging sensor 250 may optionally be configured and operable to capture video data, and not only still images data. It is noted that any feature discussed in the present disclosure with respect to images and image data acquired by imaging sensor 250 may also be extended to video. Especially, since a video can be regarded as a series of still-images, or at least contain information which enable generating of consecutive still images, it is noted that any feature discussed in the present disclosure with respect to images and image data acquired by imaging sensor 250 may also pertain to any single image of a video captured by imaging sensor 250, in relevant cases.

Figure 2:
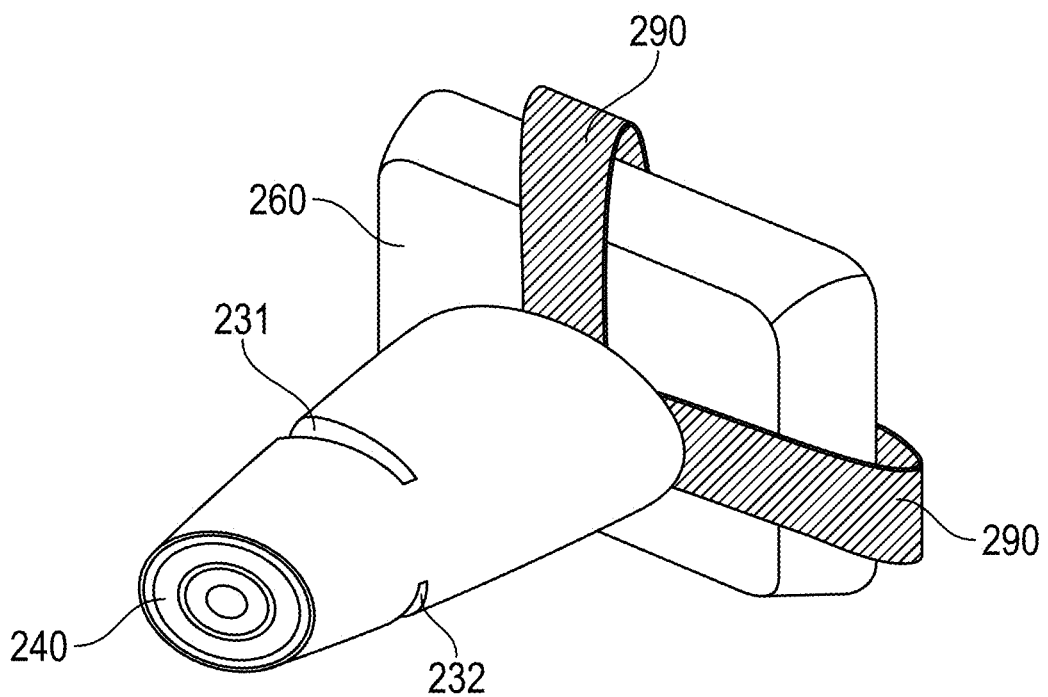
FIG. 2 is a perspective view of an example of a system for imaging of a throat of a patient, in accordance with examples of the presently disclosed subject matter.

FIG. 2 is a perspective view of an example of system 200, which is a system for imaging of a throat of a patient, in accordance with examples of the presently disclosed subject matter. In the illustrated example, system 200 includes two bite guides: a superior bite guide 231 (or "upper bite guide") shaped as a biting groove whose curvature is designed to fit maxillary dental arches dimensions of a predefined group of target patients (e.g. children between the ages of 2-4, adults, etc.), and an inferior bite guide 232 (or "lower bite guide") shaped as a biting groove whose curvature is designed to fit mandibular dental arches dimensions of the predefined group of target patients. It is noted that different bite guides 230 (such as bite guides 231 and 232) may be designed to match dental arches of different predefined group of target patients (e.g. on set of one or more bite guides 230 to match to children, and another set of one or more bite guides 230 to match to adults), on either a single mouthpiece 210, or on a plurality of interchangeable mouthpieces 210.

As illustrated in FIG. 2, system 200 may further include one or more fasteners 290 (two in the illustrated example), for mechanically detachably fastening mouthpiece 210 to an external portable handheld camera 260 in which an imaging sensor 250 (not shown in FIG. 2) is preinstalled. The detachable fastening of camera 260 to mouthpiece 210 by the one or more fasteners 290 stabilizes the imaging sensor 250 included in the external camera 260 with respect to the mouth of the patient (when the patient bites on the mouthpiece), and constrains a spatial relationship of the imaging sensor 250 with respect to mouthpiece 210 so as to provide to imaging sensor 250 via the optics of system 200 a field of view (FOV) which includes at least part of one or more tonsils of the patient, when the patient bites on the at least one bite guide. This way, imaging sensor 250 can capture an image of the throat which includes visual representation of one or more tonsils (or parts thereof).

It is noted that camera 260 may be a dedicated camera (e.g. a point-and-shoot camera or a digital single-lens reflex camera, DSLR), but this is not necessarily so, and camera 260 may be any portable device which includes optics (e.g. an objective lens) and an imaging sensor. For example, any of the following multipurpose handheld computers may serve as camera 260: smartphones, tablet computers, phablet computers, personal digital assistants (PDAs), etc.

It is noted while crosscuts of mouthpiece 210 (parallel to the coronal plane) may be circular (e.g. as exemplified in FIGS. 2 and 8), mouthpieces 210 having non-cylindrical crosscuts (e.g. oval crosscuts) may also be used, e.g. in order to better fit a shape of the mouth.

Figure 3:
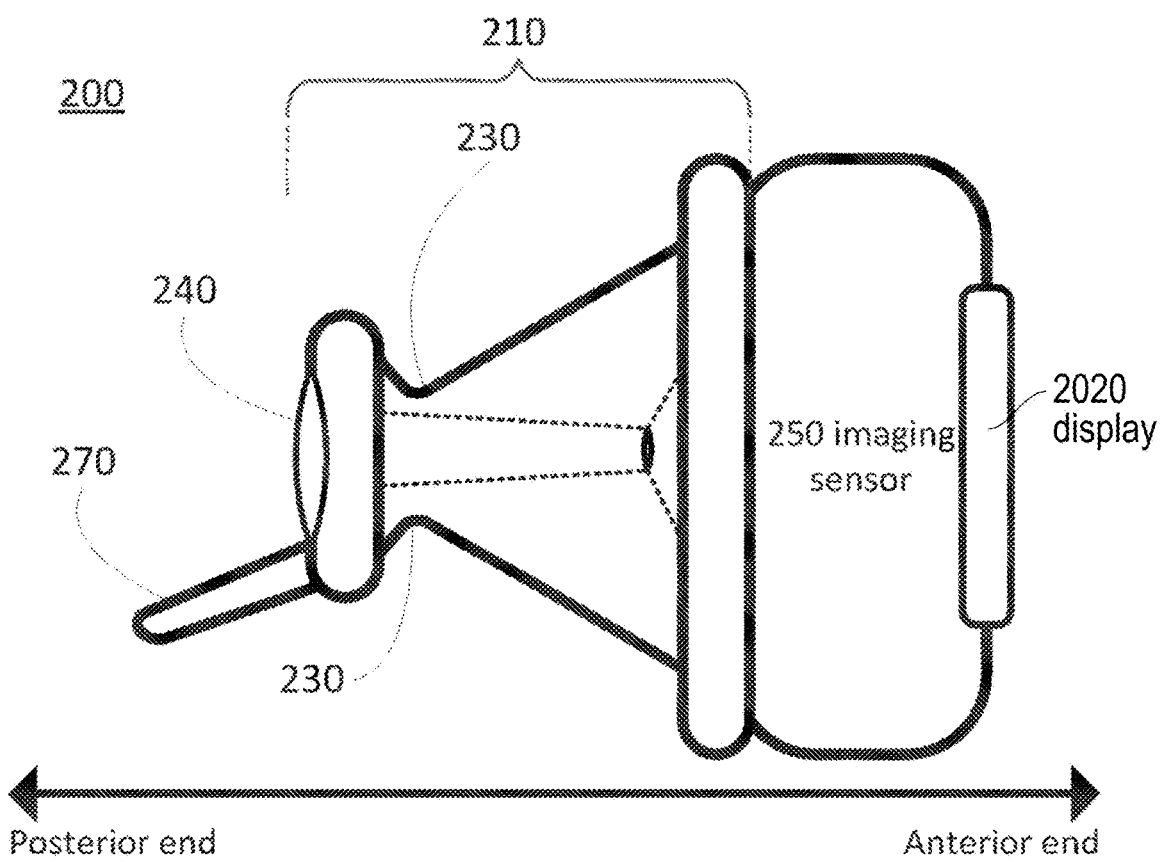
FIG. 3 is a functional block diagram illustrating an example of a system for imaging of a throat of a patient, in accordance with examples of the presently disclosed subject matter.

FIG. 3 is a functional block diagram illustrating an example of system 200, which is a system for imaging of a throat of a patient, in accordance with examples of the presently disclosed subject matter. As demonstrated in the example of FIG. 3, system 200 may optionally include tongue depressor 270 mechanically connected to mouthpiece 210 so as to enable tongue depressor 270 to depress a tongue of the patient when the patient bites on the at least one bite guide 230.

It is noted that tongue depressor 270 may be made from a rigid (or semirigid) material and be rigidly (or semirigidly) connected to mouthpiece 210, in order to transfer strength from the teeth of the patient through mouthpiece 210 (or a connected structure) to tongue depressor 270 for pushing down the tongue, when the patient bites on mouthpiece 210 and thereby stabilizes it. For example, tongue depressor 270 may be made of plastic, metal, etc. A durable material may be selected for tongued depressor 270, if a reusable tongue depressor 270 is included in system 200. It is noted that optionally, tongue depressor 270 may be detachably attached to mouthpiece 210 (e.g. to be used by adults but not but children, or for connecting different sizes of tongue depressors 270 for different audiences).

It is nevertheless noted that system 200 may be implemented without a tongue depressor (e.g. as exemplified in FIG. 1), and that optionally, the aforementioned constrained spatial relationship of intraoral optics 240 with respect to mouthpiece 210 enable the imaging sensor to image at least part of the tonsil (or tonsils) when a tongue of the patient is not mechanically forced down (or otherwise manipulated by system 200 or any other external means). Optionally, the patient may improve the field of view by pulling down (or by relaxing) her tongue, but this may not be necessarily in all implementations.

Figure 21:
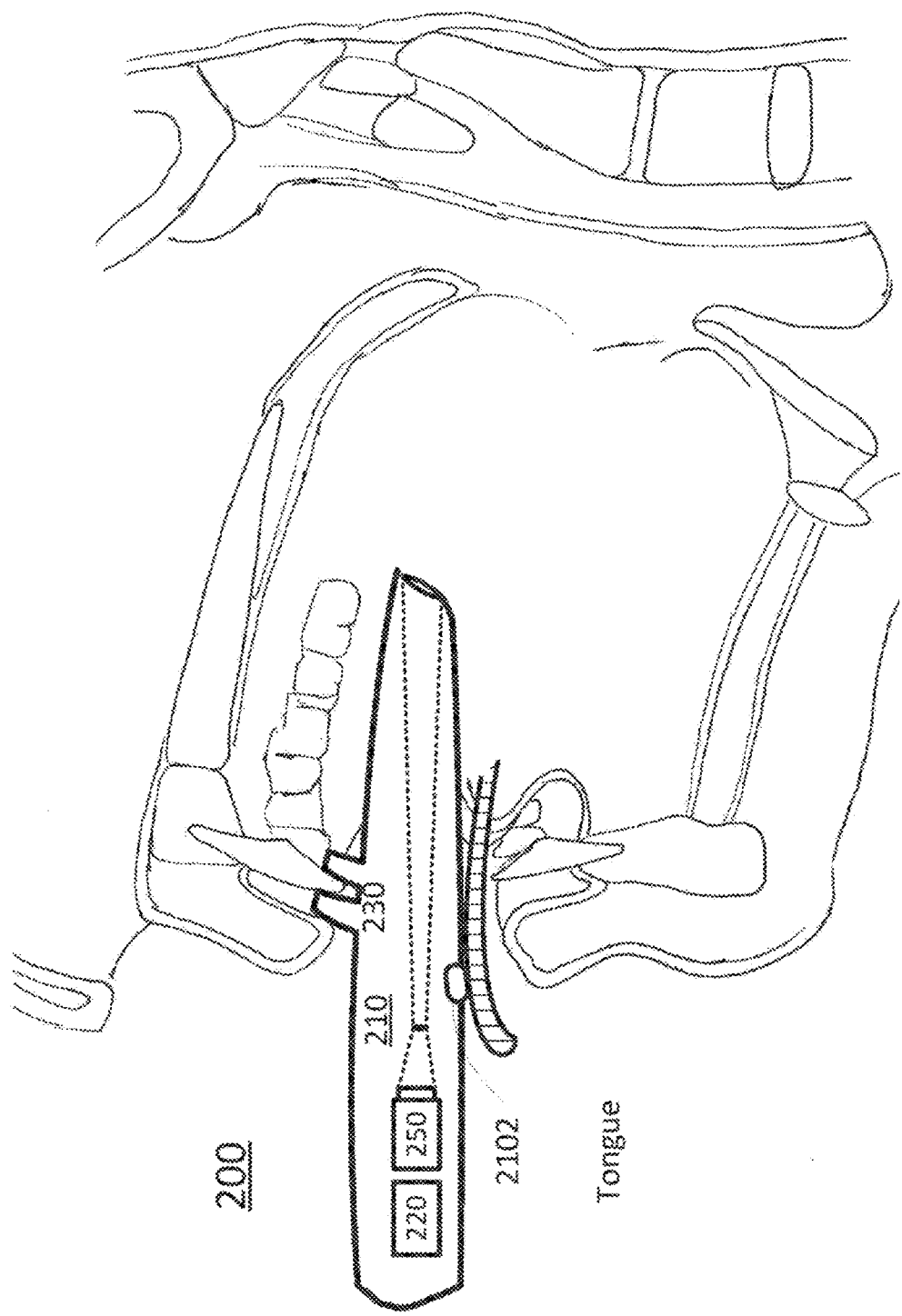
FIG. 21 is a functional block diagram illustrating an example of a system for imaging of a throat of a patient, in accordance with examples of the presently disclosed subject matter.

Referring to FIG. 21 (which is a functional block diagram illustrating an example of a system for imaging of a throat of a patient, in accordance with examples of the presently disclosed subject matter), it is noted that other positions of the tongue may also be used for clearing the tongue away from the field of view of imaging sensor 250 during acquisition. For example, system 200 may be designed such that the tongue of the patient will extend outside the mouth of the patient during the acquisition, e.g. as illustrated in FIG. 21. Processor 220 may be configured to trigger the acquisition of the image only when the tongue is extended outside the mouth. Processor 220 may be configured to trigger the acquisition of the image only when the tongue is extended outside the mouth and touches an extraoral part of system 200 (i.e. a part which is located outside the mouth of the patient during acquisition).

Optionally, system 200 may include superior bite guide 231 and inferior bite guide 232, while allowing the tongue of the patient to extend outside the mouth between mouthpiece 210 and the lower lip of the patient. Optionally, system 200 may include superior bite guide 231 and inferior bite guide 232, so that when the patient bites on bite guides 231 and 232 there is an opening between mouthpiece 210 and the lower lip of the patient, where the size of this opening is large enough for the tongue to pass through and extend outside the mouth.

Optionally, system 200 may include a sensor 2102 for detecting when the tongue extends outside the mouth, where processor 220 may use information from sensor 2102 for determining the timing of the triggering. Sensor 2102 may be, for example, a pressure sensor, a conductivity sensor, or any other electric sensor.

Referring to system 1200, it is noted that it may optionally also be shaped and configured for acquisition of intraoral images when the tongue extends outside the mouth in a similar manner, mutatis mutandis. Referring to methods 500 and 600, it is noted that any one of those methods may optionally be adapted for acquisition of intraoral images when the tongue extends outside the mouth in a similar manner, mutatis mutandis. Methods 500 and 600 may also include a stage of determining whether the tongue extends outside the mouth (e.g. based on input from a sensor such as sensor 2102), and selectively triggering the image acquisition based on result of this determining.

With respect to system 200 as a whole, it is noted that in different implementations, different components may be designed to be located inside the mouth or external to it, when the patient bites on the at least one bite guide. As to components which are located intraorally in such situations, such components may be designed to be positioned in the oral cavity proper, between a maxillary tooth (or teeth) and its corresponding mandibular tooth (or teeth), or in the vestibule (especially anteriorly to the teeth).

The mouth, consists of two regions, the vestibule and the oral cavity proper. The vestibule is the area between the teeth, lips and cheeks. The oral cavity is bounded at the sides and in front by the alveolar process (containing the teeth) and at the back by the isthmus of the fauces. Its roof is formed by hard palate and soft palate and the floor is formed by the mylohyoid muscles and is occupied mainly by the tongue.

The positioning of various components of selected components of system 200 inside or outside the mouth (and in specific positions inside the mouth or external thereto) may be determined based on various factors, such as any combination of one or more of the following considerations:

a. Weight distribution with respect to the at least one bite guide 230 (and therefore to the teeth;
b. Physical dimensions;
c. Volume, shape and/or materials of the overall intraoral part of system 200;
d. Quality potential of captured image (e.g. when deciding where to position lighting);
e. Functionality;
f. Line of Sight toward intraoral parts of interest, such as tonsils etc.
g. Sensitivity to intraoral conditions (e.g. wetness, temperature, etc.); and so on.

For example, imaging sensor 250 may be located inside the mouth or external to it, posteriorly to the teeth line, anteriorly thereto, or between corresponding maxillary and mandibular teeth.

Figure 5:
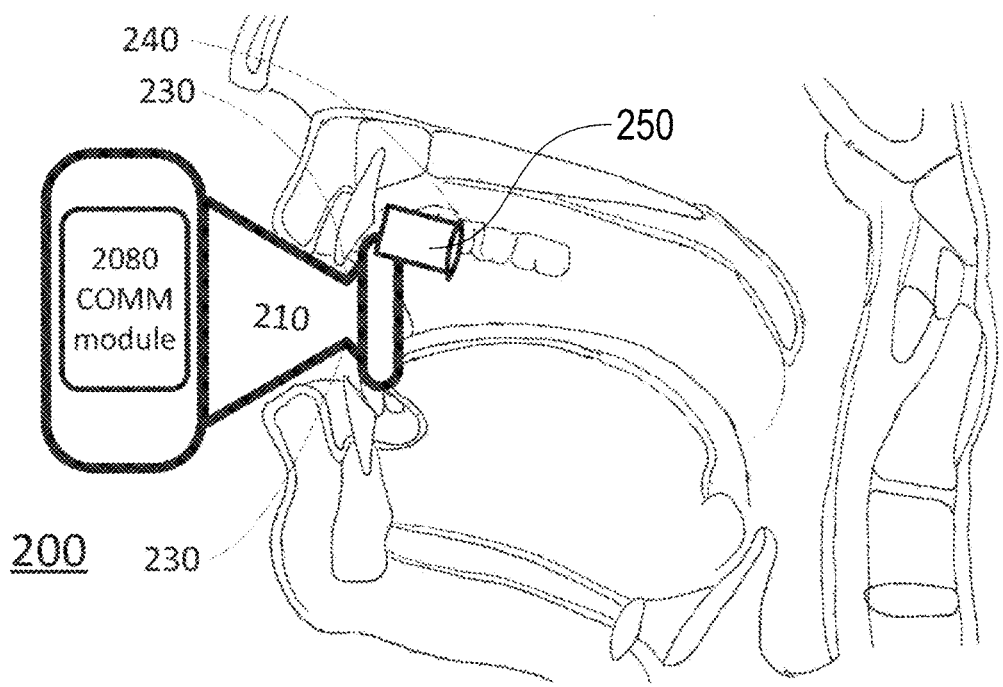
FIG. 5 is a side view diagram illustrating an example of a system for imaging of a throat of a patient located with respect to a patient who bites on bite guides of the system, in accordance with examples of the presently disclosed subject matter.

FIG. 5 is a side view diagram illustrating an example of system 200 for imaging of a throat of a patient located with respect to a patient who bites on bite guides 230 of system 200, in accordance with examples of the presently disclosed subject matter. As demonstrated in the example of FIG. 5, imaging sensor 250 may optionally be mechanically connected to mouthpiece 210 so as to constrain a spatial relationship in which imaging sensor 250 is located in the oral cavity proper of the patient during the capturing of the image. Especially, a light sensitive sensor or array (e.g. a CCD array, CMOS) of imaging sensor 250 may be located in the oral cavity proper during the time of acquisition of the image. In comparison, in the example of FIG. 3 imaging sensor 250 is located outside the mouth during the acquisition of the image of the throat. The imaging sensor 250 may also be positioned during image acquisition in the vestibule, especially anteriorly to the central incisors of the patient).

If imaging sensor 250 is located inside the mouth during the acquisition of the image, the spatial structure of system 200 may optionally be such that a center of the detection array of imaging sensor 250 is located above (i.e. supremely) the incisal ends of the maxillary central incisors of the patient. That is, optionally wherein a mechanical connection between mouthpiece 210 and imaging sensor 250 places imaging sensor 250 at the time of capturing of the image inside the mouth, such that a center of the detection array of imaging sensor 250 is located supremely to incisal ends of maxillary central incisors of the patient Intraoral optics 240 (or at least part of it) may also be positioned specifically in the oral cavity proper (e.g. posterior to an inferiormost point of any maxillary central incisor of the patient, for example as exemplified in the examples of FIGS. 1, 3 and 5). That is, optionally the mechanical connection between mouthpiece 210 and intraoral optics 240 constrains a spatial relationship of intraoral optics 240 with respect to the at least one bite guide 230 which is such that intraoral optics 240 (and at least a posteriormost optical component of which) are located in the oral cavity proper when the patient bites on the at least one bite guide 230. Therefore, the intraoral optics 240 is such case are located posteriorly to the incisors during the capturing of the image of the throat.

It is noted that the position within the oral cavity proper of various components of system 200 as constrained by respective mechanical connections of system 200 may be relatively close to the teeth. Optionally, a posteriormost part of intraoral optics 240 are located no more than 2 cm posteriorly to the incisors of the patient. Optionally, a posteriormost part of imaging sensor 250 is located no more than 2 cm posteriorly to the incisors of the patient. Optionally, the image sensitive sensor or array of imaging sensor 250 is located no more than 2 cm posteriorly to the incisors of the patient. Optionally, a posteriormost component of lighting 280 is located no more than 2 cm posteriorly to the incisors of the patient.

Having such one or more components of system 200 located in the oral cavity proper, but relatively close to the opening of the mouth may enable to capture quality images of the throat and the tonsils (or parts thereof) while still keeping system 200 very tolerable for insertion into the mouth by a wide variety of patients (even such which are reluctant to insert artificial objects deep into their mouth cavity or throat. Furthermore, such a positioning may aid in minimizing the size and/or weight of system 200, and especially of the parts of it supported by the teeth.

As suggested above, various components of system 200 may be located intraorally, but in the vestibule rather than in the oral cavity proper, when the patient bites on the at least one bite guide 230. Such components may be positioned during such biting between the teeth and the lips or the cheeks, and may include for example any one or more of the following: imaging sensor 250 (and especially a light sensitive sensor or array thereof), intraoral optics 240 (or parts thereof), lighting, one or more bite guides 230 (or parts thereof), electric circuitry, and so on.

It is noted that positioning of components of system 200 inside the mouth of the patient may differ not only in the position along the anteroposterior direction, but also in the positioning along the superoinferior direction. Specifically, some components of system 200 (e.g. lighting 280, imaging sensor 250 and especially its sensor, some or all parts of intraoral optics 240, or any combination of two or more of the above) may be located posterosuperiorly to an inferiormost point of any maxillary central incisor of the patient, when the latter bites on the at least one bite guide 230. Optionally, imaging sensor 250 is operable to capture the image when a posteriormost optical component of intraoral optics 240 is located posterosuperiorly to the inferiormost point of any maxillary central incisor of the patient. Optionally, imaging sensor 250 is operable to capture the image when a posteriormost optical component of intraoral optics 240 is located anterosuperiorly to the palatine tonsils of the patient (occasionally also called the faucial tonsils).

It is noted that if light is directed through an optical path (hereinafter referred to as "the traversing optical path") passing through mouthpiece 210 (from at least one optical components of intraoral optics 240 located in the oral cavity proper, to an imaging sensor located extraorally or in the vestibule), such a traversing optical path may be located symmetrically between the maxillary teeth and the mandibular teeth (along the superoinferior axis), but this is not necessarily so.

Optionally method 500 may include a stage, preceding stage 520, which includes obtaining image data from the imaging sensor (stills and/or video) prior to the capturing, processing the image data for recognizing at least a part of a selected body part (e.g. the tonsil, the uvula, and selectively triggering the capturing of stage 520 in response to a result of the recognizing.

Figure 6:
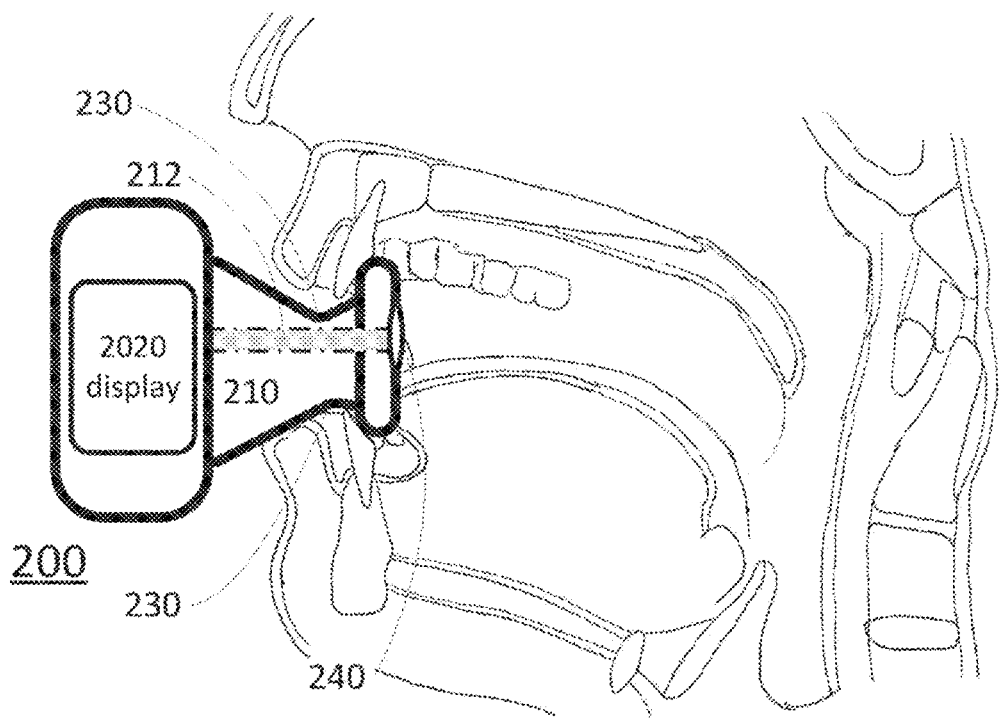
FIG. 6 is a side view diagram illustrating an example of a system for imaging of a throat of a patient located with respect to a patient who bites on bite guides of the system, in accordance with examples of the presently disclosed subject matter.

FIG. 6 is a side view diagram illustrating an example of system 200 for imaging of a throat of a patient located with respect to a patient who bites on bite guides 230 of the system, in accordance with examples of the presently disclosed subject matter.

Optionally, mouthpiece 210 may include an opening 212 through which the traversing optical path passes (at least part of this path). The opening may be hollow, but this is not necessarily so, and parts or whole of the opening may be made from a transparent (or semi-transparent) materials such as glass, plastic, and various optical polymers and co-polymers (e.g. Acrylic, Polystyrene, Polycarbonate, Cyclic Olefin Polymer (COP), Cyclic Olefin Copolymer (COC), NAS, etc.), and may include various reflecting materials (e.g. coating sides of opening 212, or serving as mirrors for deflection of light rays along the opening).

As exemplified in FIG. 6, optionally opening 212 is located closer to a top part of mouthpiece 210 than to a bottom part of mouthpiece 210. The top part of mouthpiece 210 is its part which is closer to the maxillary teeth when bitten by the patient, and the bottom part of mouthpiece 210 is its part which is closer to the mandibular teeth when bitten by the patient.

Such a configuration facilitates locating an entrance of the optical path which directs light to imaging sensor 250 relatively superiorly within the mouth, while the mouthpiece is held by the patient in a relaxed fashion between maxillary and mandibular teeth.

Figure 7:
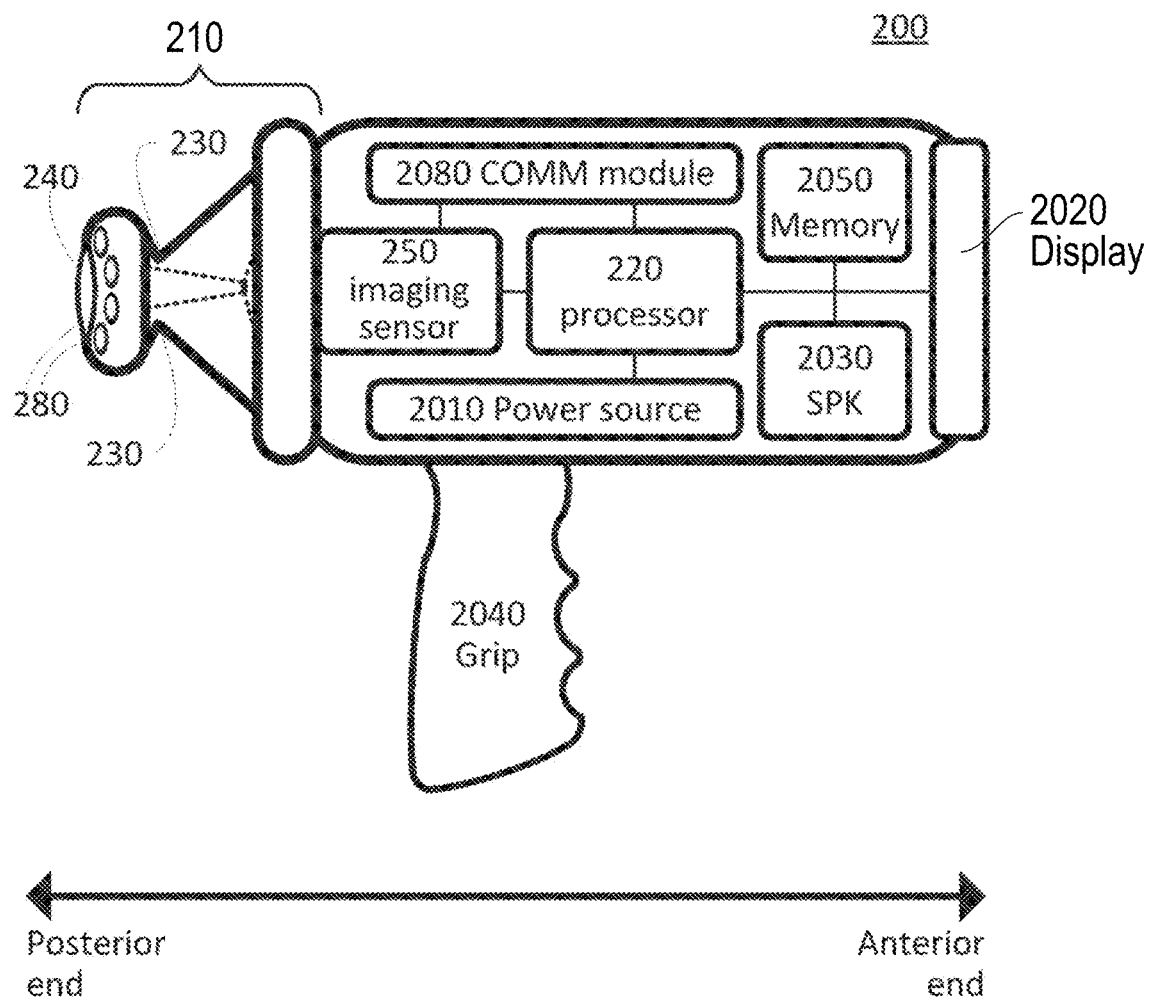
FIG. 7 is a functional block diagram illustrating an example of a system for imaging of a throat of a patient, in accordance with examples of the presently disclosed subject matter.

FIG. 7 is a functional block diagram illustrating an example of system 200, which is a system for imaging of a throat of a patient, in accordance with examples of the presently disclosed subject matter. It is noted that various optional components are illustrated in FIG. 7, and that system 200 may include any combination of one or more of the illustrated components, in addition to these discussed with respect to FIG. 1, as well as other components not illustrated in FIG. 7 (e.g. tongue depressor 270, a USB socket, etc.).

As aforementioned, system 200 may be designed to be used by the patient herself, or by another person. As exemplified in FIG. 7, system 200 may further include at least one handgrip 2040 for gripping of system 200 by the patient (using one or both hands), for carrying the system 200 by the patient to a position in which the patient can bite on the at least one bite guide 230. As shown in the illustrated example, the one or more handgrip 2040 may be designed to ergonomically facilitate holding and moving of system 200 by a patient located next to its posterior end (which is ought to be inserted into the mouth of the patient). It is noted that handgrips designed to be used by a person other than the patient may also be used (in addition or instead of this designed for the patient), as well as generic handgrips which may be used by either the patient or another person. It is noted that the one or more handgrips 2040 (if implemented) are not necessarily external to mouthpiece 210, and handgrips 2040 may also be designed by shaping mouthpiece 210 to include a topography (e.g. various indentations) which facilitate gripping or holding of the system by a person.

It is noted that if the patient inserts mouthpiece 210 partially into her own mouth, sometimes it may be hard for her to tell if system 200 is positioned correctly in her mouth (i.e. in a way which enables capturing a quality image of the throat, or an image which meets other predefined criteria such as light level, focusing level, etc.). Therefore, a user interface may be included in system 200, for indicating to the user (whether it's the patient or another operator) when system 200 is properly held by the patient, as well as other messages (if so configured). For example, such a user interface may be a speaker 2030, a monitor 2020, light emitting diode (LED) indicators, and so on. Other messages to the user may pertain to the time in which the patient need to hold the mouthpiece in her mouth, to the direction in which it should correct the positioning of the mouthpiece in her mouth, and so on.

Generally, system 200 may include a user interface operable to indicate to the patient when a location of mouthpiece 210 enables capturing of the image by imaging sensor 250.

System 200 may also include processor 220, which is operable to receive data from one or more sensors, to process it, and to transmit various messages based on the results of the processing. For example, processor 220 may be operable to receive information from any one of the following sensors: imaging sensor 250, piezoelectric sensors, light-level indicators, user interfaces (e.g. press button, touch screen), and so on. Additional information which may be used for the processing of processor 220 is, for example, information received through communication module 2080 from an external system (e.g. from a computer operated by a medical professional in a remote location).

Based on the processing of information obtained, processor 220 may issue messages to various components of system 200. For example, it can instruct imaging sensor 250 when to acquire images and which image acquisition parameters to use; it can decide which images include sufficient details of the throat or parts thereof (e.g. tonsils), and to send such one or more images via communication module 2080 to an external system, and so on.

It is noted that processor 220 may be implemented as dedicated hardware processor (designed specifically for the functionalities of system 200), implemented, for example, as a digital signal processor (DSP), a microcontroller, a field programmable gate array (FPGA), an application specific integrated circuit (ASIC), or any combination of two or more thereof. Processor 220 may be implemented as a hardware processor (whether dedicated or not), firmware processor, software processor, or any combination thereof.

It is noted that system 200 may include more than one processor (e.g. more than one chip, for example, a controller, a processor in charge of imaging sensor 250, a processor in charge of communication module 2080, and/or a controller in charge of display 2020, and so on). As a matter of convenience, all such processors (if more than one is implemented) are collectively referred to as "processor 220".

For example, optionally processor 220 may be configured and operable to trigger capturing of the image by imaging sensor 250 in response to information received from at least one detector of system 220. Information that would lead to triggering of image acquisition may arrive from any combination of one or more of the above identified sensors, and/or from other sensors.

Optionally, processor 220 may be operated to process image date (stills or video) collected by imaging sensor 250 in order to recognize a selected body part (e.g. tonsil, uvula) or part thereof, and to selectively trigger capturing of the image by imaging sensor 250 in response to results of the processing. For example, processor 220 may trigger the capturing of the image after it recognized that at least half of a tonsil is visible by imaging sensor 250.

It is noted that the image of the throat acquired by system 200 may be used for diagnosis of various medical conditions (whether throat specific or inflicting other areas as well). For example, some such medical conditions include: sore throat, tonsillitis (an infection in the tonsils), pharyngitis (inflammation of the pharynx), strep throat, mononucleosis, gastric reflux, and so on.

Processor 220 may be configured and operable to: (a) process one or more images acquired by imaging sensor 250 for deciding whether predefined conditions relating to one or more specific medical conditions (e.g. sore throat, tonsillitis, pharyngitis, strep throat, mononucleosis, gastric reflux) are met, and (b) selectively control transmission of images which meet the predefined conditions to a remote system via communication module 2080.

It is noted that various image processing algorithms which are known in the art may be used for analyzing the acquired images by processor 220, such as edge detection, color comparison, image comparison, and so on. Many image processing algorithms for analysis of inspected image of the human body are known in the art, and may be used for the purpose of the present application, as will be clear to a person who is of skilled in the art. For example, few such algorithms are described in the article "Image Processing for Skin Cancer Features Extraction" by Md. Amran Hossen Bhuiyan, Ibrahim Azad, Md. Kamal Uddin, published in International Journal of Scientific & Engineering Research Volume 4, Issue 2, February 2013, which is incorporated here in its entirety by reference, and which may be implemented herein mutatis mutandis.

It is noted that processor 220 may be located in a casing of mouthpiece 210, or immediately connected thereto (and not, for example, by a data cable without any mechanically stable physical connection). Optionally, a distance between processor 220 and a posteriormost bite guide 230 of system 200 is smaller than 10 centimeters.

Figure 4:
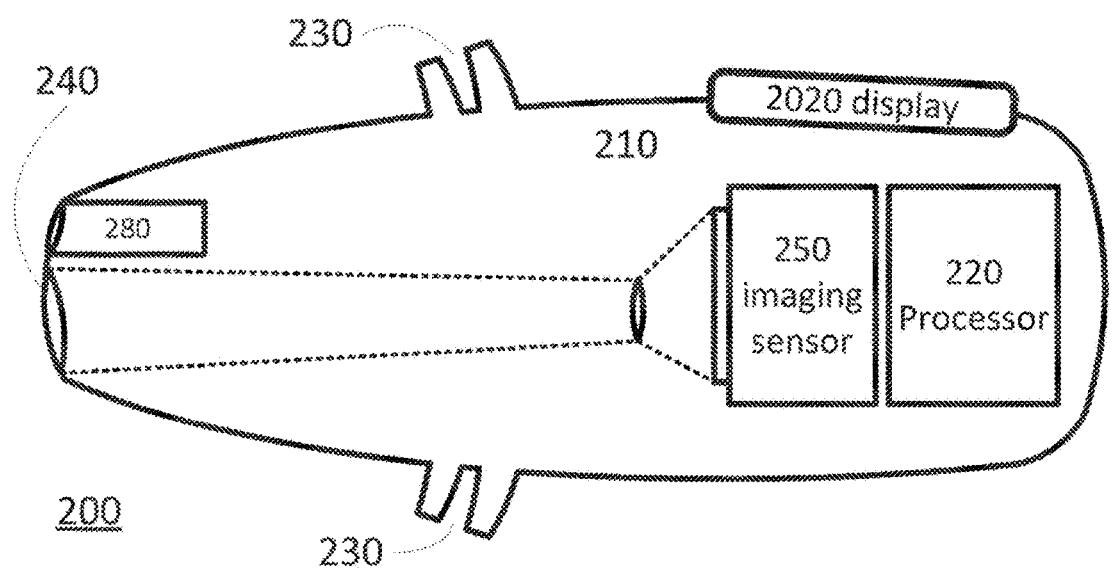
FIG. 4 is a functional block diagram illustrating an example of a system for imaging of a throat of a patient, in accordance with examples of the presently disclosed subject matter.

Referring to lighting 280, which is used to cast light into the mouth and/or throat of the patient, it is noted that such lighting may be located intraorally or extraorally. Lighting 280 may include a single light source (e.g. as exemplified in FIG. 4), or a plurality of light sources (e.g. ex exemplified in FIG. 7). The one or more light sources of lighting 280 may be a Light-emitting diode (LED) light sources, or any other type of light sources which can be incorporated into a handheld portable system such as system 200, many such types are known in the art. Lighting 280 may be configured to provide continuous light. Lighting 280 may be configured to provide flash light of short duration.

System 200 may optionally include display 2020 (also referred to as monitor 2020), which is operable to display images. Optionally, display 2020 may be operable to display images concurrently to the capturing of the image by the imaging sensor (when the patient bites onto system 200), but this is not necessarily so. Optionally, display 2020 may be configured and operable to display images which are based on image data captured by imaging sensor 250, and especially images of the throat of the patient. It is noted that display 2020, if implemented, may optionally be mechanically connected to the mouthpiece, so that its weight may be supported by the mouthpiece when held by the teeth of the client, thereby not requiring holding system 200 by hands at all times.

Displaying of images captured by imaging sensor 250 on display 2020 (and especially images of the throat) may be used for diagnosis, for improving image quality and/or getting a better view of the throat (by providing a reference for the person operating system 200), and so on. It is noted that optionally, processor 220 may provide additional visual information for display 2020 to be displayed on display 2020—either together with the image data of imaging sensor 250, or separate therefrom.

For example, additional layers of information may be overlaid above the image of the throat. For example, display 2020 (or another user interface output) may be use to display instructions indicative of a way in which the user should change a state of system 200 (e.g. move system 200), so as to enable acquisition of the image of the throat of the patient. This may be achieved, for example, by displaying For example, the display may be used to display arrows indicating to which direction system 200 should be moved to obtain a better view of the tonsils. In another example, the display may be used to display information which is indicative of whether sufficient light is available for the acquisition of the image or not. It is noted that visual instructions for a required change in a state of the system may be provided not only by a screen, but may also be provided by one or more dedicated visual aids (e.g. LEDs, shaped lights, etc.).

Other information which may be displayed on display 2020 is system 200 (e.g. power level, status, etc.), information received from a remote system (e.g. diagnosis and/or instructions of a medical expert, videoconference which such an expert), and so on. If an external camera 260 is connected to mouthpiece 210, display 2020 may be a display of the external camera 260 (e.g. of a cellphone, or a DSLR camera). Information from a remote system to be displayed on monitor 2020 may be obtained by communication module 280.

System 200 may include a user interface (e.g. display 2020, a speaker, etc.) for providing instructions to the patient to carry out one or more actions which are intended to clear the optical path between the lens and the tonsils (or other parts of the throat). Such actions may result in lower of the tongue by the patient. Such actions may include, for example, placing the tongue outside the mouth, uttering a specific sound, etc. he instructions may be textual, verbal, and may also include playing the sound which should be uttered by the patient. The method may include instructing execution of at least one action by the patient for clearing an optical path between the intraoral optics and the tonsil (such as the actions discussed above).

It is noted that display 2020 may be located in a casing of mouthpiece 210, or immediately connected thereto (and not, for example, by a data cable without any mechanically stable physical connection). Optionally, a distance between display 2020 and a posteriormost bite guide 230 of system 200 is smaller than 10 centimeters.

It is noted that optionally, instead of (or in addition) to displaying information on display 2020, processor 220 may provide display information (e.g. images, video, text) to an external system via communication module 280, for displaying on a monitor of the external system. For example, if a display of system 200 is located in an anterior end of the system and therefore is not viewable by the patient when system 200 is in her mouth (or if system 200 does not have a display at all), the image of the throat (or other visual information) may be sent to a cellular phone of the patient, to be presented to her in a comfortable manner.

Referring to communication module 2080, it is noted that communication module 2080 may be configured and adapted to communicated with an external system over a wired connection (e.g. a data cable such as a USB cable), over wireless communication channel (e.g. Wi-Fi connection or Bluetooth connection), or both. If communication module 2080 is operable for wireless communication, it can serve as a wireless communication module. Furthermore, communication module 2080 may be operable to communicate with a remote system in an intermediated manner, via one or more intermediating communication systems. For example, communication between communication module 2080 and the remote system (which may be, for example, a computer used by a medical expert located in a different city) may be routed over a cellular telephony network, in which case it is intermediated by a series of communication system of the cellular network providers.

System 200 may also include memory unit 2050, which may include one or more tangible memory units and/or intangible memory units. Memory unit 2050 may be used to store images acquired by imaging sensor, processed images processed by processor 200 based on image data acquired by imaging sensor 250, information received from an external system via communication module 2080, operational parameters and data used by processor 220 or other components, and so on.

Optionally, system 200 may include power source 2010 for providing energy (e.g. in the form of electricity) to other component of system 200.

Figure 8:
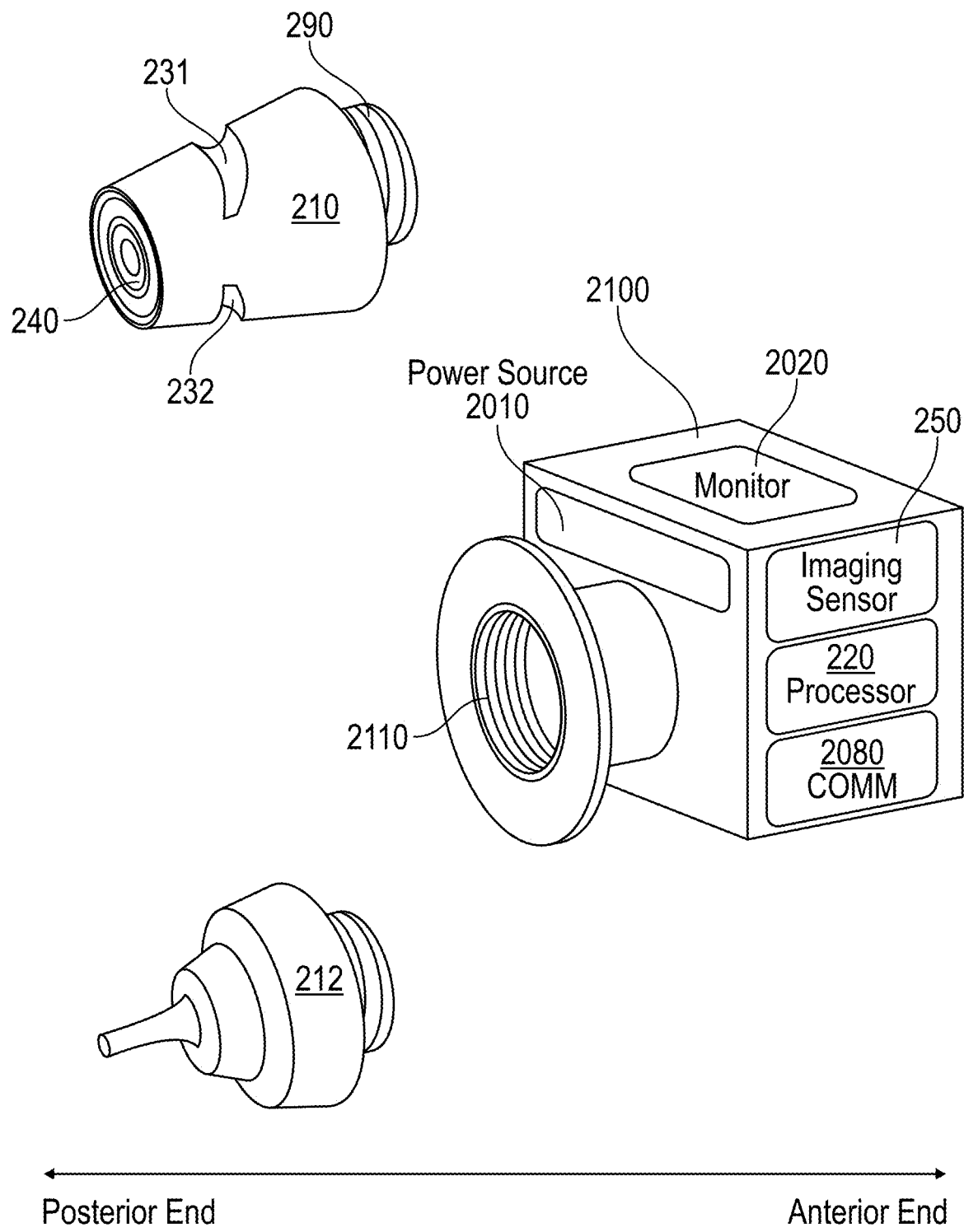
FIG. 8 is a functional block diagram illustrating an example of a system for imaging of a throat of a patient, in accordance with examples of the presently disclosed subject matter.

FIG. 8 is a functional block diagram illustrating an example of system 200, which is a system for imaging of a throat of a patient, in accordance with examples of the presently disclosed subject matter. It is noted that system 200 may be used for imaging other parts of the patient in addition to the throat and/or mouth. Especially, system 200 may be used for imaging inside other body orifices, such as the ears, the nostrils, the rectum, and the vagina, and/or the skin of the patient.

Optionally, system 200 may include a casing 2100 which includes imaging sensor 250 and possibly other components of system 200 as well. Casing 2100 includes at least one mechanical fastener 2110 for connecting of specula used for investigating body orifices.

Mouthpiece 210 in such case is separable from casing 2100, and it includes at least one fastener 290 for mechanically detachably fastening mouthpiece 210 to the at least one mechanical fastener 2110 of casing 2100. It is noted that many connection mechanisms may be used for fasteners 290 and 2100. Few examples of such connection mechanisms are a magnet, a vacuum suction cup, hook and loop fasteners ("Velcro"), glue, screws, nuts and bolts, friction, pressure, etc. The many other connection mechanisms known in the art may also be used.

In addition to mouthpiece 210 (which may be used for imaging inside the mouth body orifice), system 200 further includes at least one speculum for examination of a body orifice selected from the group consisting of: ear, nostril, rectum, and vagina. In FIG. 8 speculum 212 which is an ear speculum, thereby enabling acquisition of images from inside the ears, such as images of the ear canal and of tympanic membrane. This may be used to facilitate treatment and management of the patient's ear conditions, like otitis media.

It is noted that if system 200 includes additional speculum (or specula), or at least includes one or more fasteners 2110 for connecting external specula, imaging sensor 250 may be further configured and operable to capture an image of the body orifice when the respective speculum is at least partly inserted into a respective body orifice of the patient. It is noted that components of system 200 which support the image acquisition in the mouth (e.g. lighting 280) may also be used for acquisition of images in other body orifices, or alternatively that equivalent components may be included in system 200, mutatis mutandis.

Optionally, casing 2100 may include power source 2010 for providing energy (e.g. in the form of electricity) to other component included within casing 2100, or to units connected thereto (e.g. connected using a USB connection).

Figure 9:
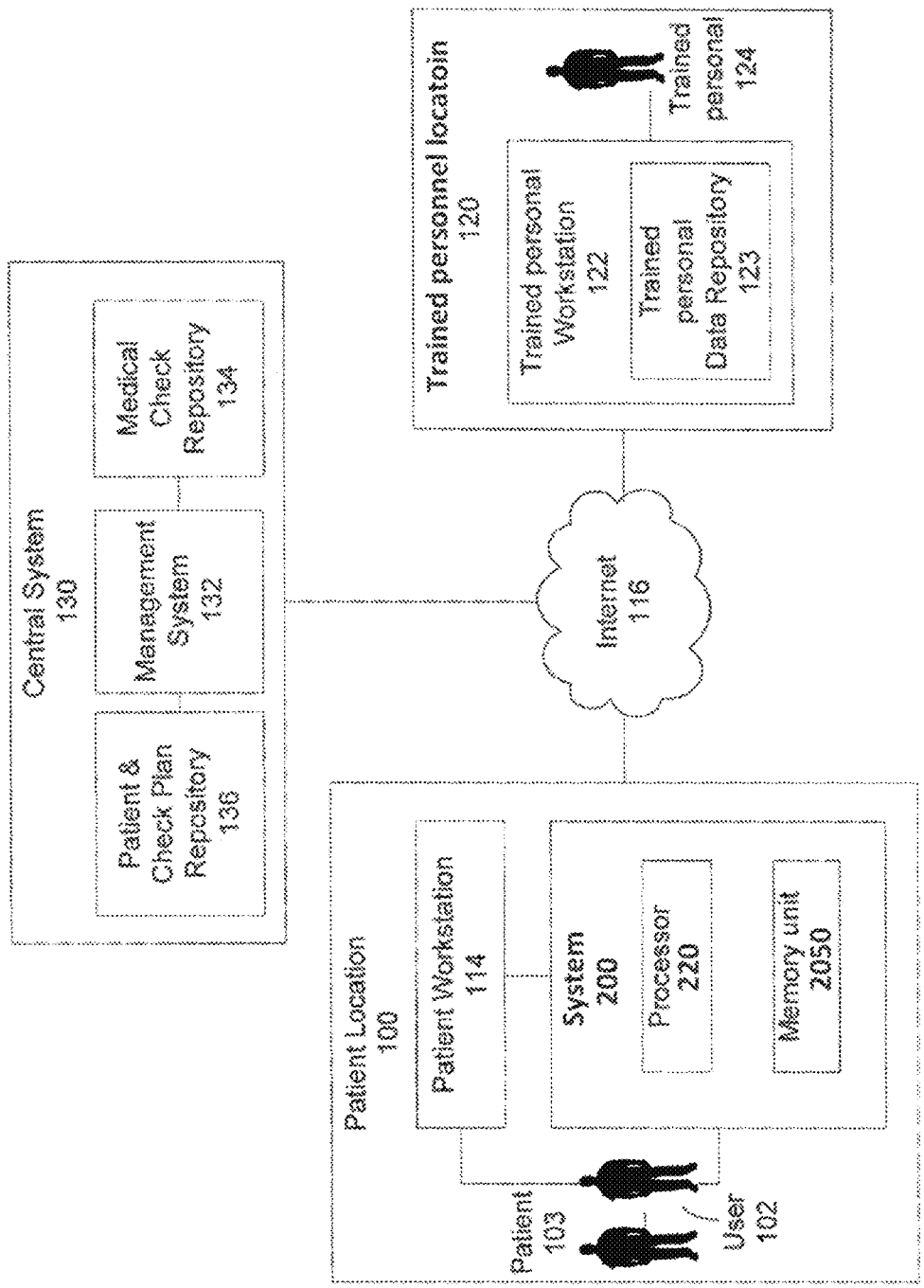
FIG. 9 is a block diagram schematically illustrating an architecture of a system for performing a self-guided medical examination, in accordance with examples of the presently disclosed subject matter.

FIG. 9 is a block diagram schematically illustrating an architecture of a system for performing a self-guided medical examination, in accordance with examples of the presently disclosed subject matter. It can be appreciated that user 102 and patient 103 are located at patient location 100. User 102 can in some cases be patient 103 whose medical examination is required (in such cases, even though user 102 and patient 103 are shown as separate entities in the drawings, they are in fact the same entity). In other cases, user 102 can be a person that will be performing the medical examination of patient 103.

For the purpose of performing a medical examination, user 102 operates system 200 as a diagnostic device, as further detailed below. In some cases, user 102 also operates a patient workstation 114, as further detailed below. Patient workstation 114 can be any computer, including a personal computer, a portable computer, a cellular handset or an apparatus with appropriate processing capabilities, including a computer and/or an apparatus which can be, for example, specifically configured for that purpose. It is to be noted that in some cases, patient workstation 114 can be incorporated within system 200. System 200 may include (or is otherwise associated with) at least one processor 220 (e.g. digital signal processor (DSP), a microcontroller, a field programmable gate array (FPGA), an application specific integrated circuit (ASIC), etc.) and a memory unit 2050 (e.g. ROM, hard disk, etc.). Processor 220 may be configured to receive instructions and control the components and operations of system 200.

In some cases system 200 can be configured to communicate with patient workstation 114. The communication between system 200 and patient workstation 114 can be realized by any communication means, e.g. via wired or wireless communication. It can be noted that user 102, patient 103, system 200 and patient workstation 114 are located at patient location 100.

System 200 can be configured to acquire various data as discussed above, and especially image data (e.g. of the throat of the patient). The acquired data can be transmitted (directly from system 200 or through patient workstation 114) to trained personnel workstation 122 located at trained personnel location 120 and/or to central system 130. Central system 130 and trained personnel workstation 122 can be any computer, including a personnel computer, a portable computer, a cellular handset or an apparatus with appropriate processing capabilities, including a computer and/or an apparatus which can be, for example, specifically configured for that purpose. The acquired data can be transmitted for example via Internet 116. It is to be noted that the data can be transmitted while utilizing other known communication alternatives, such as a cellular network, VPN, LAN, etc. It is noted that central system 130 may be located in the same building as system 200, but this is not necessarily so, and it may even be located in another city or in another country. Likewise, trained personnel location 120 may be located in the same building as system 200 (and/or in the same building as central system 130), but this is not necessarily so, and it may even be located in another city or in another country.

Central system 130 includes patient & check plan repository 136 in which varied data relating to the patient is maintained. Such data can include, for example, patient identification number, patient name, patient age, patient contact details, patient medical data (such as diseases, sensitivities to medicines, etc.), check plans data (as further detailed below), etc. Central system 130 can further include a medical examination repository 134 in which data acquired by system 200 and patient workstation 114 is maintained. Such data can include, for example, results of medical examinations performed using diagnostics device (such as ear readings, lungs or heart recorded sound, blood pressure, body temperature, etc. as further detailed below). Central system 130 further includes management system 132 configured to forward received data to a selected trained personnel workstation 122 (for example an available trained personnel workstation 122 or trained personnel workstation 122 with the shortest queue).

It is to be noted that when providing a central system, there may be more than one trained personnel location 120 and trained personnel 124 as central system 130 allows for a distributed approach in which data can be received by the central system 130 from multiple patient locations and transferred by it to multiple trained personnel locations. Thus, in case the transmitted data is received at central system 130, the data is saved in medical examination repository 134 and management system 132 can transmit the received data to trained personnel location 120 (e.g. via Internet 116. It is to be noted that the data can be transmitted while utilizing other known alternatives, such as a cellular network, VPN, LAN, etc.). In some cases, management system 132 can also manage other processes such as, subscribing patients, planning scheduling of patients to available trained personnel, etc.

It is to be noted that central system 130 is optional to the solution and that central system 130 can be part of the trained personnel system 120, In addition the communication between the patient location 100 to the trained personnel location 120 can be implemented directly without the use of or need for a central system 130.

When the transmitted data (e.g. images of the throat of the patient) is received at trained personnel workstation 122, the data can be saved in trained personnel data repository 123 that can be connected to trained personnel workstation 122. A trained personnel 124 (e.g. a doctor, a nurse, a medic, etc., including any other person with the know-how and skill to acquire and/or analyze medical data), located at trained personnel location 120, can retrieve and review the acquired data, for example using trained personnel workstation 122. It is to be noted that patient workstation 114, trained personnel workstation 122 and central system 130 can include a display (e.g. LCD screen), and a keyboard or any other suitable input/output devices. In some cases, trained personnel 124 can provide feedback to user 102, for example by transmitting data back to patient workstation 114. Such feedback can include, for example, analysis of the received data, request to receive more data, medical treatment instructions, invitation to further examination, etc. Alternatively or additionally, trained personnel 124 can transmit feedback data to central system 130, which, in turn, can transmit the feedback data to patient workstation 114 (e.g. via the Internet, cellular network, etc.).

It is noted that system 200 may transmit to the trained personnel varied medical data, e.g. images from various body orifices or of the skin, as well as other medically significant data (e.g. temperature, humidity, recorded sounds, etc.).

Figure 10:
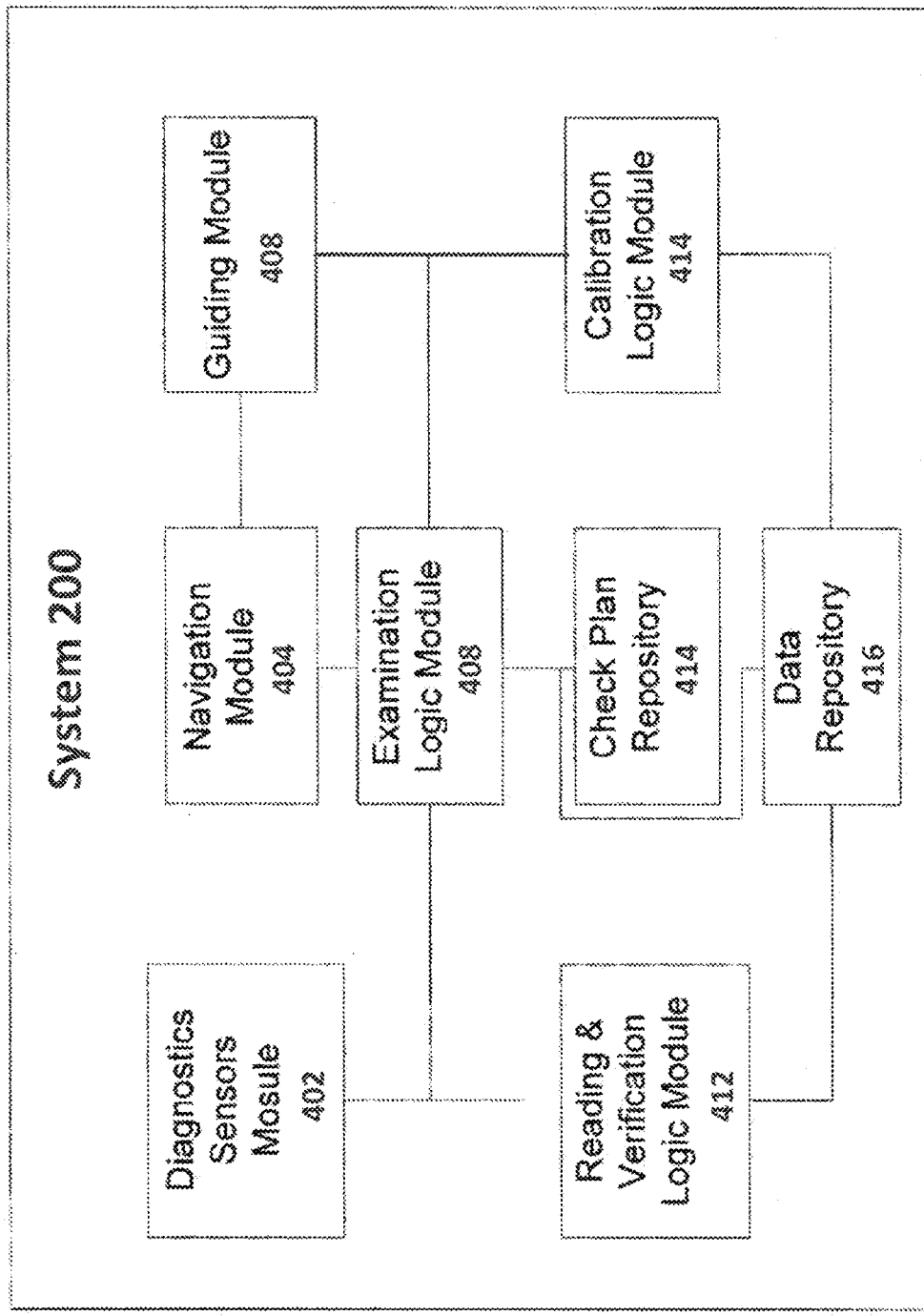
FIG. 10 is a block diagram schematically illustrating one example of a system as a diagnostic device which is configured to perform medical examination of the patient, in accordance with examples of the presently disclosed subject matter.

FIG. 10 is a block diagram schematically illustrating one example of system 200 as a diagnostic device which is configured to perform medical examination of the patient, in accordance with examples of the presently disclosed subject matter. System 200 may optionally include, inter alia, diagnostic sensors module 402, guiding module 406, examination logic module 408, check plan repository 410, and data repository 416. Out of these components, data repositories may be implemented on memory 4050, and processing module may be implemented as part of processor 420. System 200 can further include navigation module 404, reading and verification logic module 312 and calibration logic module 414. It is noted that system 200 may include various combinations of these components, and does not necessarily have to include all of them (if any).

Examination logic module 408 can be responsible for operating system 200 for performing a medical examination of patient 103. System 200 can be activated for example by User 102. Upon activation, user 102 can optionally indicate the patient to be checked. Such indication can be in the form of inputting patient 103 identification details (e.g. patient id, patient name, etc.), for example in patient workstation 114. In other cases such indication can be in the form of selecting a specific patient 103, for example from a list of known patients. Such list of known patients can be displayed on patient workstation 114. In some cases, such list of known patients can be displayed on a display connected to system 200. Details of known patients to be presented on such list of known patients can be retrieved, for example, from one or more of: data repository 416, check plan repository 410, trained personnel data repository 123, patient & check plan repository 136 or any other location operatively connected to system 200 on which patient data is stored. In further cases system 200 can automatically identify patient 103 by using methods of body identification such as face recognition, fingerprint reading or any other mean of biometric identification. Such automatic identification can utilize, for example, navigation camera 420 or any other peripheral, reader or sensor connected to system 200 or to patient workstation 114 that enable acquiring data relevant to the automatic identification. It is to be noted that other methods of indicating or identifying a patient to be checked can be utilized as well.

In some cases, after receiving patient 103 details, examination logic module 408 can be configured to retrieve data relating to a check plan. Such check plan data can be stored on one or more of: check plan repository 410, patient & check plan repository 136, trained personnel data repository 123 or any other location operatively connected to system 200 on which patient specific check plan data can be stored. A check plan can define a series of medical examinations and data to be acquired by system 200. Such medical data acquisition can be performed by user 102 on patient 103. The medical data can include, for example, body temperature, blood pressure, pulse, respiratory rate, throat image, mole image, ear image, etc. The check plan can in some cases be a generic check plan (e.g. a series of medical examinations that can be standard pre-determined medical examinations). In other cases the check plan can be defined according to a certain medical condition of patient 103 (e.g. a check plan for patients with cancer can include a series of cancer specific required medical examinations, a check plan for patients with high blood pressure can include a series of high blood pressure specific required medical examinations, etc.). In further cases, the check plan can be specifically defined for patient 103, for example according to a trained personnel 124 decision (e.g. a physician interested in monitoring specific medical data of a specific patient can decide upon a patient specific check plan). The check plan can include information, inter alia about the examination process, steps and logic, and predefined reading parameters such as type of sensor to be used (still image vs. video), required length of reading (sound or video recording) in terms of time (e.g. seconds), and reading data thresholds (for example definition of acceptable minimal and/or maximal reading limits to be used as a quality parameter of a reading.

Upon retrieval of the check plan to be performed, examination logic module 408 can be configured to utilize navigation module 404 in order to enable determination of current diagnostics device spatial disposition with respect to patient's 103 body (or a specific part thereof).

It is to be noted that the term spatial disposition or the like can relate to spatial distances, spatial angles (including orientations), or any other spatial reference that is used for characterizing a spatial relationship between two objects, e.g. between system 200 and patient's 103 body (or a specific part thereof).

Navigation module 404, if implemented, is responsible for the operation of various sensors utilized for that purpose. Navigation module 404 can utilize pre-stored reference data for establishing data about system 200 current and desired spatial dispositions with respect to patient's 103 body (or a specific part thereof, e.g. her mouth). The pre-stored reference data can consist of image based reference data and/or system 200 spatial disposition based reference data, or any other relevant reference data, including data that can be read by system 200 navigation module 404 or diagnostic sensors 402. The reference data can be for example images of patient 103 (external patient images and/or internal patient images of internal body parts), general organ images, device coordinates, data of relativity between spatial dispositions with respect to patient's 103 body (or a specific part thereof), etc. Such pre-stored reference data can be stored on patient & check plan repository 136, trained personnel data repository 123 or any other location operatively connected to system 200 on which image based reference data is stored. Upon establishment of system 200 current spatial disposition with respect to patient's 103 body (or a specific part thereof), navigation module can calculate a route to a desired system 200 spatial disposition with respect to patient's 103 body (or a specific part thereof), that can be defined, for example, by the patient specific check plan. The route calculation can be performed continuously or periodically (e.g. every predetermined time interval), for example until arrival to the desired system 200 spatial disposition with respect to patient's 103 body (or a specific part thereof).

In some cases, examination logic module 408 can be configured to utilize guiding module 406 in order to provide various guidance data instructing user 102 how to maneuver system 200 to the desired system 200 spatial disposition with respect to patient's 103 body (or a specific part thereof). Such guidance data can include, inter alia, voice commands, image display, system 200 vibrations, etc.

Such guidance data can be presented to user 102 continuously or periodically (e.g. every pre-determined time interval), until system 200 arrives at the desired spatial disposition with respect to patient's 103 body (or a specific part thereof, from which the medical examination can be performed. Such guidance data can be calculated according to the respective calculation of a route to the desired system 200 spatial disposition with respect to patient's 103 body (or a specific part thereof), as calculated by navigation module 404.

Upon arrival to the desired system 200 spatial disposition with respect to patient's 103 body (or a specific part thereof), for example as indicated by the patient specific check plan, examination logic module 408 can be configured to utilize reading and verification logic module 412 in order to acquire medical data of patient 103. Upon arrival to desired system 200 spatial disposition with respect to patient's 103 body (or a specific part thereof), reading and verification module 412 can be configured to verify that system 200 is located at the desired spatial disposition with respect to patient's 103 body (or a specific part thereof) when acquiring medical data of patient 103.

Reading and verification module 412 can be further configured to instruct diagnostics sensor module 402 to prepare to acquire medical data of patient 103, and to perform acquisition of such medical data, as further detailed below, inter alia with reference to FIG. 14. After acquisition of medical data of patient, reading and verification module 412 can be configured to verify that the acquired data meets pre-defined standards (e.g. a required length of reading, reading data thresholds, etc.). In case the acquired data does not meet the pre-defined standards, system 200 can in some cases be configured to instruct user 102 to perform the required repositioning and reorienting thereof in order to bring system 200 to the desired spatial disposition with respect to patient's 103 body (or a specific part thereof). Following repositioning and reorienting of system 200, reading and verification logic module 4012 can be configured to retry acquiring the medical data of patient 103.

System 200 can be further configured to utilize diagnostics sensor module 402 that can be configured to acquire medical data of patient 103. Diagnostics sensor module 402 can be responsible for the operation of various sensors used for acquiring various medical data of patient 103. Such medical data of patient 103 can be used for example for diagnostics by trained personnel 124. Diagnostics sensor module 402 is further discussed below, inter alia with reference to FIG. 11.

In some cases, system 200 can further include a calibration logic module 414. Calibration logic module 414 can be configured, inter alia, to acquire reference data relating to medical examinations of patient 103. In some cases, the reference data is acquired by system 200 during an initial calibration performed by trained personnel 124. For example, a physician can perform a medical examination of patient 103 and system 200 can, for example, record the medical examination performed by trained personnel 124, including the acquired medical data. The recorded data, including the acquired medical data, can be stored, for example, on one or more of: check plan repository 410, patient & check plan repository 136, trained personnel data repository 123 or any other location operatively connected to system 200 on which data relating to patient 103 can be stored. It is to be noted that system 200 can further include data repository 416. Data repository 416 can be configured to store various data, including, inter alia, data relating to one or more patients and various medical data thereof (e.g. data acquired during a medical examination of the patients), as further detailed below.

In some cases, diagnostics device can further include check plan repository 210. Check plan repository 410 can be configured to store various data, including, inter alia, data relating to patient specific check plans, as further detailed below.

Figure 11:
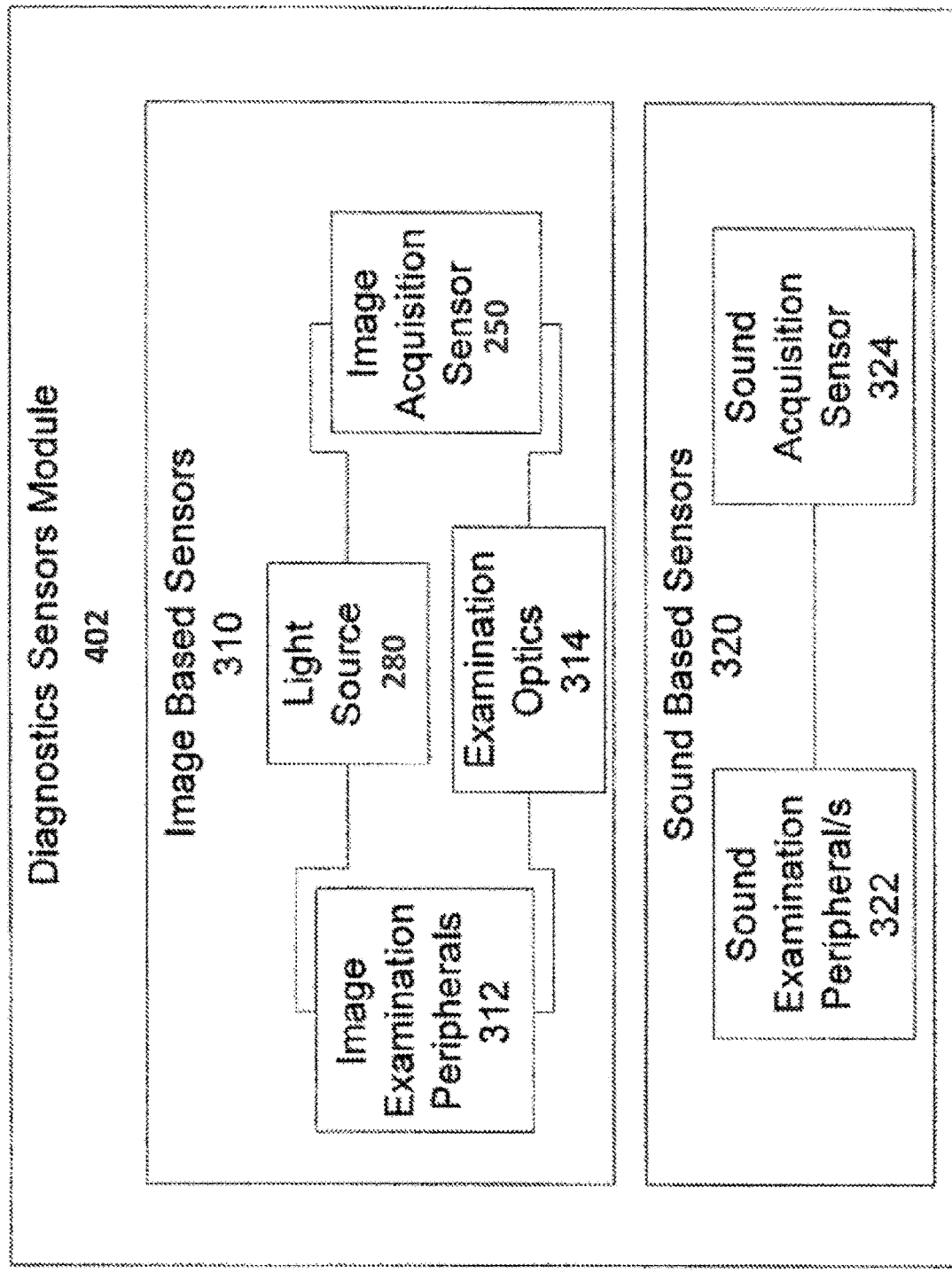
FIG. 11 is a block diagram schematically illustrating an example of diagnostic sensors configured to acquire medical data, in accordance with examples of the presently disclosed subject matter.

FIG. 11 is a block diagram schematically illustrating an example of diagnostic sensors configured to acquire medical data, in accordance with examples of the presently disclosed subject matter. Diagnostics sensors module 402 can include, inter alia, image based sensors 310, sound based sensors 320, as well as other sensors not shown in the drawing. Diagnostic sensors 402 can be designed for taking a specific organ reading (such as mouth image reading, as discussed above) and general organ readings (such as external skin reading, eye reading, etc.). Diagnostic sensors 402 can be modular e.g. some sensors can be attached/detached to diagnostic device 104, in accordance with the required medical examination.

Image based sensors 310 can include one or more light sources 280. Light sources 280 can be Light Emitting Diodes, or any other light source known in the art. Light sources 280 can be utilized for example to light the areas of which an image is to be acquired in order to provide for sufficient image quality (e.g. a quality that will enable image analysis by trained personnel 124).

Image based sensors 310 can further include image examination peripherals 312. Image examination peripherals 312 can include, inter alia, various components that enable safe access to various body parts, such as a human ear, throat, etc. Such components can be, for example, made of plastic and can be attached to system 200. Such components can, for example, have a generic physical structure that fits various body parts regardless of the fact that different people, at different ages, have different body parts structure (e.g. a child has a smaller ear than a grown person and the image examination peripherals 312 can be designed to fit substantially any ear structure, etc.). Image examination peripherals 312 can aid user 102 in positioning the system 200 in the desired spatial disposition with respect to patient's 103 body (or a specific part thereof so that acquisition of image based medical data can be performed. Image based sensors 310 can further include imaging sensor 250. Imaging sensor 250 can be based on standard sensors such as complementary metal oxide semiconductor (CMOS) or charged couple device (CCD) or any other applicable sensor known in the art. Optionally, imaging sensor 250 can be designed to fit image acquisition of multiple body parts or organs, regardless of size or distance (e.g. it can have the required resolution and/or size and/or light sensitivity to fit multiple body parts or organ readings). It is to be noted that imaging sensor 250 can be the same sensor as the navigation image acquisition sensor (if implemented), and vice versa.

Image based sensors 310 can further include examination optics 314.

Examination optics 314 can be, for example, camera lenses. Examination optics 314 can be designed to fit various wavelengths, field depth, wide or narrow lens angle, etc. and therefore can fit various types of image readings as well as various types of organ sizes and structures. Examination optics 314 enable image acquisition sensor 250 to acquire image based medical data, having the required properties (e.g. examination optics 314 should enable acquisition of an image that covers the entire area that is required for analysis by trained personnel 124, etc.). In some cases, data acquired from examination optics 314 and image acquisition sensor 250 can be later analyzed and/or transformed and/or aligned to fit the specific required organ area reading (e.g. in order to fit a quality analysis by trained personnel 124, the specific required image area can be cut of the entire image or can be aligned using image analysis and or image transformation or manipulation techniques and/or algorithms known in the art).

Sound based sensors 320 can include one or more sound acquisition sensors 324. Sound acquisition sensors 324 can be, for example, a microphone, or any other device capable of acquiring sound data. Sound acquisition sensors 324 can fit multiple sound frequencies that can be adjusted to fit recording of specific organ sound (as, for example, heart sound frequencies are different than lung sound frequencies). Sound acquisition sensors 324, can also include various abilities to assist acquiring a quality sound such as noise cancellation filters, etc.

Sound based sensors 320 can further include sound examination peripherals 322.

Sound examination peripherals 322 can include, inter alia, various components that enable easy fit, comfortable adjustment and safe access to various body parts, such as a human chest, stomach, lung, etc. Such components can be, for example, made of plastic, rubber, etc. and can be attached to system 200. Such components can, for example, have a generic physical structure that fits various body parts regardless of the fact that different people, at different ages, have different body parts structure (e.g. a child has a smaller chest than a grown person and the sound examination peripherals 322 can be designed to fit substantially any chest structure, etc.). Sound examination peripherals 322 can aid user 102 in positioning system 200 in the desired spatial disposition with respect to patient 103 body (or a specific part thereof) in a way that will enable acquisition of sound based medical data (e.g. allow minimizing any external noise that can interfere with the sound acquisition).

Revering to FIG. 9, it is noted that optionally, patient workstation 114 can further include patient location camera (not illustrated) and/or patient location microphone (not illustrated), that can be used, inter alia, for acquiring image (including video) and/or sound data of patient 103. Such data can be used by trained personnel 124 for example for viewing and/or hearing patient 103 and/or user 102 and/or system 200 by trained personnel 124 as well as allowing video conferencing, as further detailed below. It is to be noted that in some cases, patient workstation 114 can be incorporated within system 200.

As detailed above, in some cases system 200 can be configured to communicate with patient workstation 114. The communication between system 200 and patient workstation 114 can be realized by any communication means, e.g. via wired or wireless communication. It can be noted that user 102, patient 103, system 200 and patient workstation 114 are located at patient location 100.

It is to be noted that central system 130 is optional to the solution and that central system 130 can be part of any trained personnel system 120, In addition the communication between trained personnel workstation 122 and system 200 and/or patient workstation 114 (also referred to hereinafter as: "TP-patient connection") can be implemented directly without the use of, or need for, a central system 130. It is also to be noted that TP-patient connection can be implemented using a distributed approach i.e. multiple patients can be served by one trained person and/or one patient can be served by multiple trained persons. In such case, patient workstation 114 can include for example a local repository containing one or more connections information to a relevant trained personnel workstation 122, and vice-versa.

When the transmitted data (including image and/or voice data of patient 103) is received at trained personnel workstation 122, the data can be displayed on trained personnel workstation 122. For that purpose, trained personnel workstation 122 can include, inter alia, a display (e.g. LCD screen). It is to be noted that the image and voice data of patient 103 can be streamed to trained personnel workstation 122. Trained personnel 124 can view the received data on display and provide user 102 with navigational directions for navigating system 200 to a desired spatial disposition with respect to patient's 103 body (or a specific part thereof, e.g. mouth, throat, ear) from which medical data is to be acquired. For this purpose, trained personnel workstation 122 can include a camera (not illustrated) and/or a microphone (not illustrated) that can be used for acquiring image (including video) and/or sound data of trained personnel 124. It is to be noted that during the TP-patient connection a video conference can take place while utilizing, for example, the cameras and microphone in both patient workstation 114 and trained personnel workstation 122.

For the purpose of providing instructions to user 102, trained personnel 124 can provide such instructions to user 102, which are transmitted to patient workstation 114 or to system 200. Patient workstation 114 or system 200 can be configured to present the instructions to user 102, for example visually on a display (e.g. LCD screen included in patient workstation 114 or system 200). Another exemplary alternative is to present the instructions to user 102 vocally while translating the received data to voice commands (using known methods and techniques).

Upon arrival to a desired system 200 spatial disposition with respect to patient's 103 body (or a specific part thereof), trained personnel 124 can instruct user 102 to bite on bite guides 230, and/or to acquire medical data using system 200. In addition, trained personnel workstation 122 and/or guiding device 1124 can enable trained personnel 124 to acquire the required medical data by themselves. In such a case, trained personnel workstation 122 will transfer trained personnel 124 instruction to system 200, which will automatically acquire the required readings based on the received instructions (when the patient bites on the at least one bite guide 230, if imaging the throat, or otherwise if imaging other body parts).

It is to be noted that trained personnel workstation 122 system 200 can also be configured to use the predefined reading acquisition parameters, as defined in check plan repository 210 and/or patient and check plan repository 136 or any other location operatively connected to trained personnel workstation 122 and/or system 200 on which patient data is stored. After medical data is acquired, diagnostics device can be configured to transmit the acquired data to trained personnel workstation 122 and/or to central system 130. When the transmitted data is received at trained personnel workstation 122, the data can be saved in trained personnel data repository 123 that can be connected to trained personnel workstation 122. Trained personnel 124 (e.g. a doctor, a nurse, a medic, etc., including any other person skilled to analyze the transmitted data), located at trained personnel location 120, and/or at central system 130, can retrieve and review the acquired data, for example using trained personnel workstation 122. It is to be noted that patient workstation 114, trained personnel workstation 122 and central system 130 can include a display (e.g. LCD screen), and a keyboard or any other suitable input/output devices. In some cases, trained personnel 124 can provide feedback to user 102, for example by transmitting data back to patient workstation 114. Such feedback can include, for example, analysis of the received data, request to receive more data, medical treatment instructions, invitation to a further examination, etc. Alternatively or additionally, trained personnel 124 can transmit feedback data to central system 130, which, in turn, can transmit the feedback data to patient workstation 114 (e.g. via the Internet, cellular network, etc.).

FIG. 12A is a functional block diagram illustrating an example of bitable camera stabilization system 1200, in accordance with examples of the presently disclosed subject matter.

FIG. 12B is a functional block diagram illustrating an example of bitable camera stabilization system 1200, when connected to external portable handheld camera 3000, in accordance with examples of the presently disclosed subject matter.

Bitable camera stabilization system 1200 includes at least the following components:
a. Bitable support 1210 which includes at least one bite guide 1230 for stabilizing bitable support 1210 with respect to teeth of the patient when the patient bites on the at least one bite guide 1230.
b. Intraoral optics 1240 operable to collect light from the throat of the patient and to direct the light towards an internal optical path 1212 intrinsic to bitable support 1210. Intraoral optics 1240 is mechanically connected to bitable support 1210 in a mechanical connection which constrains a spatial relationship of intraoral optics 1240 with respect to bitable support 1210 so that when the patient bites on the at least one bite guide 1230: intraoral optics 1240 is stabilized by bitable support 1210 inside a mouth of the patient, having a field of view which includes at least part of a tonsil of the patient.
c. At least one fastener 1290 for mechanically detachably fastening bitable support 1210 to an external portable handheld camera 3000 which includes imaging sensor 3500, so as to create an optical path between intraoral optics 1240 and imaging sensor 3500, the optical path including internal optical path 1212 and an external optical path 3012 passing within portable handheld camera 3000.

It is noted that bitable camera stabilization system 1200 may be part of system 200. Especially, bitable support 1210 may serve as mouthpiece 210, the one or more bite guides 1230 may serve as the one or more bite guides 230, intraoral optics 1240 may serve as intraoral optics 240, and one or more fasteners 1290 may serve as the optional one or more fasteners 290 of system 200.

For reasons of brevity and clarity, the discussion relating to any one or these components of system 200 is not repeated in full with respect to these aforementioned corresponding components of system 1200. It is noted that all of the discussion offered above with respect to any one of the components of system 200 (including functionally, shape and size, material, variations, interrelation between components, and so on) is relevant to the corresponding component of system 1200.

Especially: (a) all of the discussion offered above with respect to mouthpiece 210 is applicable, mutatis mutandis, to bitable support 1210; (b) all of the discussion offered above with respect to the at least one bite guide 230 is applicable, mutatis mutandis, to at least one bite guide 1230; (b) all of the discussion offered above with respect to intraoral optics 240 is applicable, mutatis mutandis, to intraoral optics 1240; and (d) all of the discussion offered above with respect to the at least one fastener 290 is applicable, mutatis mutandis, to the at least one fastener 290.

For similar reasons of brevity and clarity, the discussion relating to any one or the components of external portable handheld camera 260 is not repeated in full with respect to external portable handheld camera 3000, and the discussion relating to imaging sensor 250 is not repeated in full with respect to imaging sensor 3500. It is noted that all of the discussion offered above with respect to any one of these two components of system 200 (including functionally, shape and size, material, variations, interrelation between components, and so on) is relevant to the corresponding component of system 1200.

System 1200 is a portable handheld system. That is, the physical dimensions of system 1200, as well as its weight and the materials it is made of, enable a person to carry it on her person unassisted, and to operate it without any external mechanical support. System 1200 is therefore sufficiently small and light to be operated while held in one or both hands (or in some cases, as will be demonstrated below, held by the teeth of the patient). Depending on its designated target audience, system 1200 may be designed to be sufficiently small and light to be handled by an unassisted child.

Like system 200, system 1200 may be used by the patient herself for imaging her own throat (whether for her own use, or to be used by another person or system, such as a medical personal or a medical system). However, system 1200 may also be used for imaging the throat of the patient by another person.

FIG. 12C is a functional block diagram illustrating an example of bitable camera stabilization system 1200, when connected to external portable handheld camera 3000 and when the patient bites on the bite guides 1230 of system 1200, in accordance with examples of the presently disclosed subject matter.

Figure 13B:
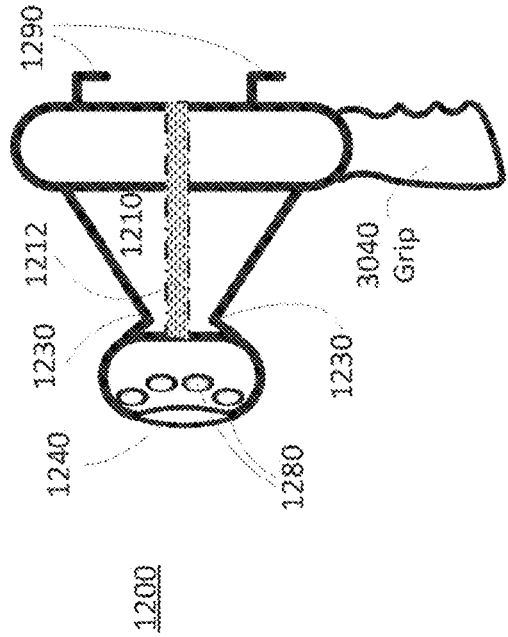
FIGS. 13A, 13B and 13C are functional block diagrams illustrating examples of bitable camera stabilization systems, in accordance with examples of the presently disclosed subject matter.
Figure 13C:
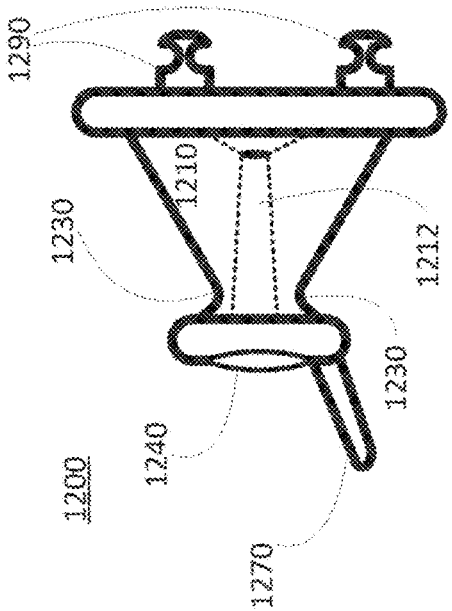
Figure 13A:
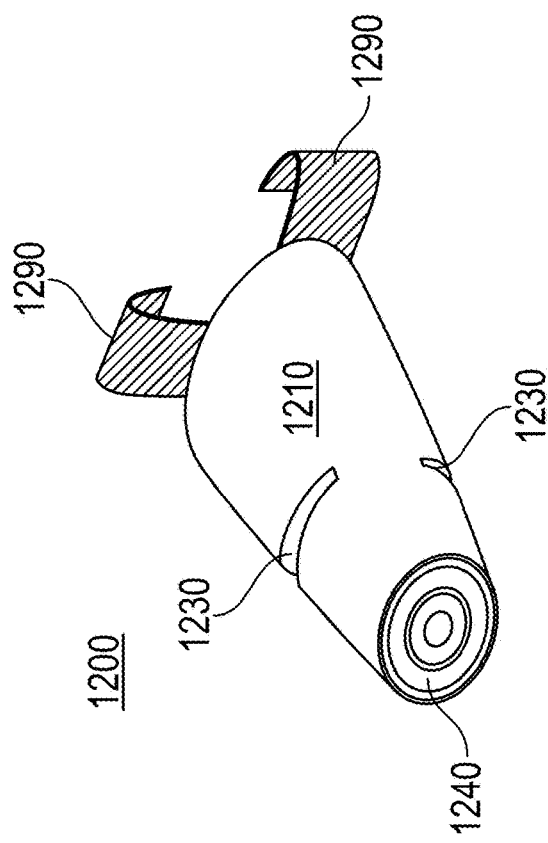

FIGS. 13A, 13B and 13C are functional block diagrams illustrating examples of bitable camera stabilization system 1200, in accordance with examples of the presently disclosed subject matter.

Figure 14:
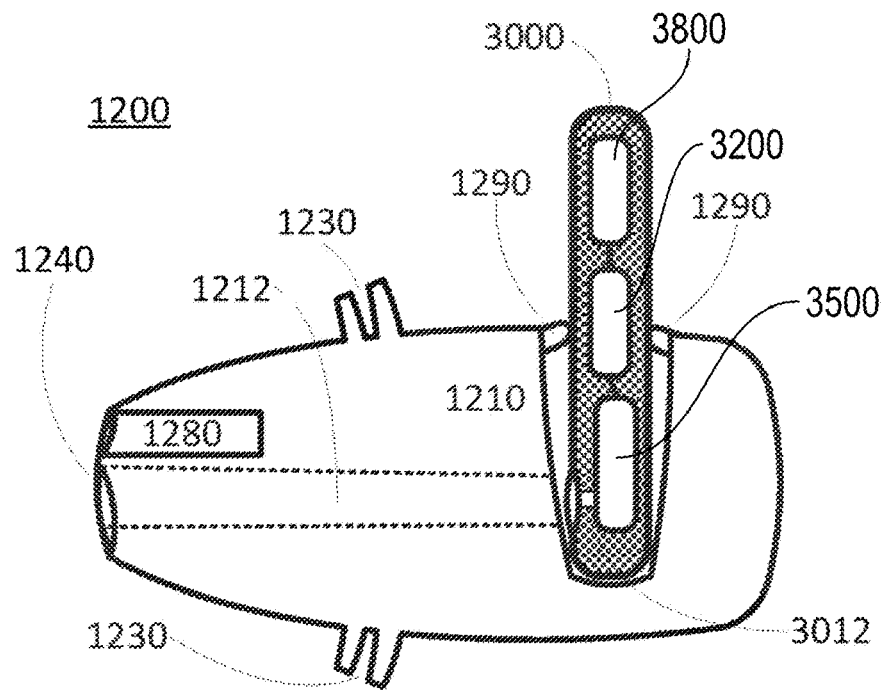
FIGS. 14 and 15 are functional block diagrams illustrating examples of bitable camera stabilization systems, when connected to external portable handheld camera 3000, in accordance with examples of the presently disclosed subject matter.
Figure 15:
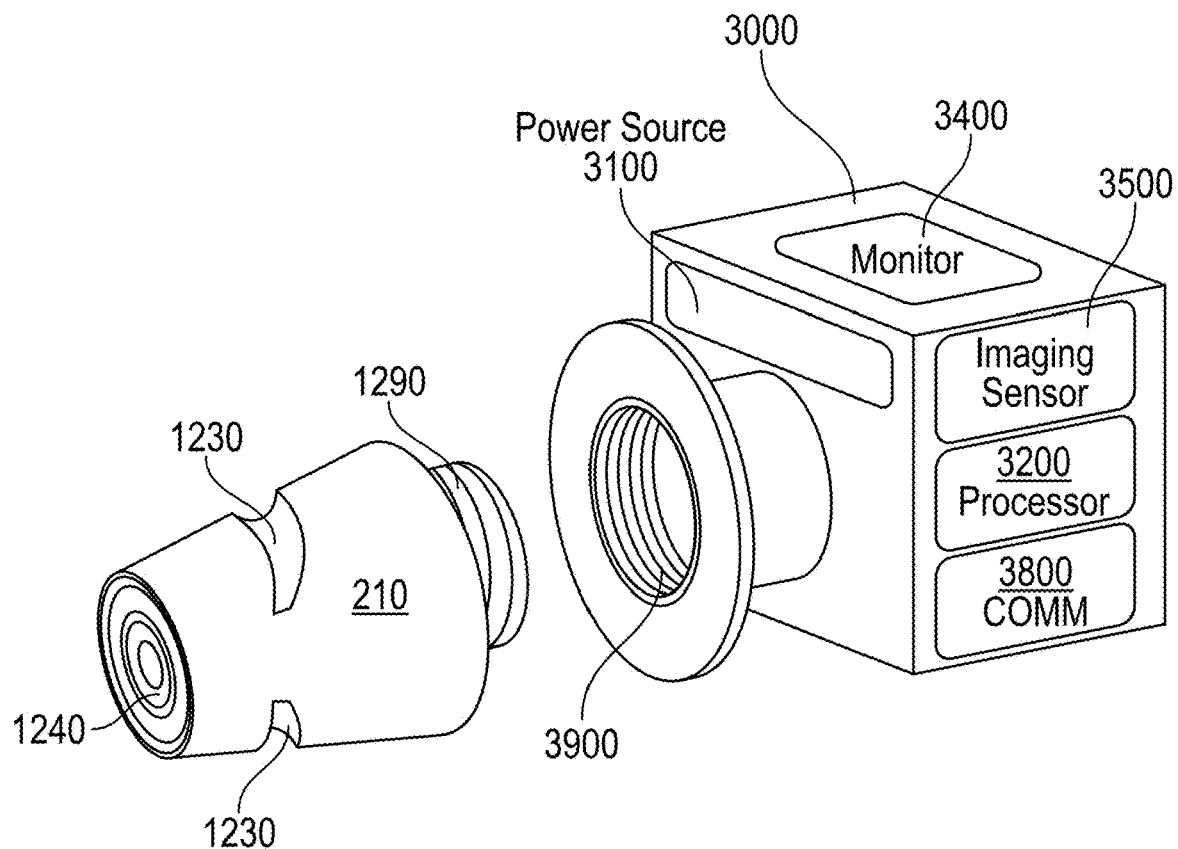

FIGS. 14 and 15 are functional block diagrams illustrating examples of bitable camera stabilization system 1200, when connected to external portable handheld camera 3000, in accordance with examples of the presently disclosed subject matter.

Optionally, at least one fastener 1290 is operable to mechanically detachably fasten bitable support 1210 to external portable handheld camera 3000 for stabilizing its imaging sensor 3500 with respect to the at least one bite guide 1230, so that when the patient bites on the at least one bite guide 1230, imaging sensor 3500 is stable with respect to a throat of the patient.

Optionally, the spatial relationship of intraoral optics 1240 with respect to bitable support 1210 constrained by the mechanical connection between the two, enables intraoral optics 1240 to collecting light arriving from at least part of the tonsil of the patient when a tongue of the patient is not mechanically forced down.

Optionally, system 1200 may further include tongue depressor 1270 which is mechanically connected to bitable support 1210 so as to enable tongue depressor 1270 to depress a tongue of the patient when the patient bites on the at least one bite guide 1230. It is noted that all of the discussion offered above with respect to the tongue depressor 270 is applicable, mutatis mutandis, to tongue depressor 1270.

Optionally, he mechanical connection between bitable support 1210 and intraoral optics 1240 constrains a spatial relationship of intraoral optics 1240 with respect to the at least one bite guide 1230 such that intraoral optics 1240 are located in the oral cavity proper of the patient when the patient bites on the at least one bite guide.

Optionally, the mechanical connection between bitable support 1210 and intraoral optics 1240 constrains a spatial relationship of intraoral optics 1240 with respect to the at least one bite guide such that a posteriormost optical component of intraoral optics 1240 is located posterosuperiorly to an inferiormost point of any maxillary central incisor of the patient when the patient bites on the at least one bite guide 1230.

Optionally, system 1200 may further include handgrip 3040 which is connected to bitable support 1210 and which is operable to be used for carrying system 1200 by the patient to a position in which the patient can bite on the at least one bite guide 1230. It is noted that all of the discussion offered above with respect to the handgrip 2040 is applicable, mutatis mutandis, to handgrip 3040.

Optionally, an internal optical path 1212 is located closer to a top part of bitable support 1210 than to a bottom part of the bitable support 1210.

Optionally, system 1200 may include lighting 1280. All of the discussion offered above with respect to lighting 280 is applicable, mutatis mutandis, to lighting 1280.

Optionally, camera 3000 may include processor 3200. All of the discussion offered above with respect to processor 220 is applicable, mutatis mutandis, to lighting processor 3200. It is noted that, while not illustrated, system 1200 may also include a processor, e.g. for controlling operation of one or more components of system 1200.

Optionally, camera 3000 may include communication module 3800. All of the discussion offered above with respect to communication module 2080 is applicable, mutatis mutandis, to communication module 3800.

Optionally, camera 3000 may include at least one mechanical fastener 3900 for connecting to one or more fasteners 1290 of system 1200.

Optionally, system 1200 and/or camera 3000 may include a power source (e.g. power source 3100), for providing energy (e.g. in the form of electricity) to other component of the respective unit.

Optionally, camera 3000 may include a monitor 3400. All of the discussion offered above with respect to monitor 2020 is applicable, mutatis mutandis, to monitor 3400.

Referring to system 200 and/or to system 1200, it is noted that optionally, the system may include one or more bearing to which at least one optical component of the intraoral optics is connected and which enable to move that at least one optical component inside the mouth with respect to the mouthpiece of the system, when the patient bites onto the bite guide. This may be used, for example, in order to allow scanning within the mouth, in order to acquire visual data from a larger field of view. The acquisition of image data may be executed when the relevant components of intraoral optics is positioned in different locations and/or orientations within the mouth of the patient.

For example, such a bearing (or bearings) may be used to enable horizontal scan within the oral cavity, vertical scan within the oral cavity, circular or elliptical scan within the oral cavity, or other types of scanning.

The movement of the intraoral optical component may be done manually by an operator of the system (whether the patient or another user), e.g. by a handle that extends beyond the mouthpiece. The movement of the intraoral optical component may be done by the system itself, using one or more engines and one or more controller, which can operate together in order to move the at least one optical component of the intraoral optics with respect to the mouthpiece of the system.

FIG. 16 is a flow chart illustrating an example of method 500, in accordance with examples of the presently disclosed subject matter. Method 500 is a method for imaging of a throat of a patient. Referring to the examples set forth with respect to the previous drawings, method 500 may be executed by system 200. It is noted that for the reason, together with aiming for brevity and clarity of the disclosure, the description of method 500 does not repeat all the details variations discussed with respect to system 200. It is therefore noted that every functionality, detail and variation discussed with respect to system 200 (and the various components of which) may be implemented as part of method 500, mutatis mutandis.

Method 500 includes at least stage 510 and stage 520.

Stage 510 includes stabilizing intraoral optics with respect to a mouth of the patient, by a mouthpiece which is coupled to the intraoral optics and which is stabilized with respect to the mouth by teeth of the patient which bite on at least one bite guide. It is noted that both the intraoral optics and the mouthpiece are parts of a portable handheld system.

The intraoral optics and the mouthpiece may be fixed parts of such a portable handheld system, but one or more of those components (the intraoral optics and the mouthpiece) may be detachably attached to other components of the portable handheld system. Those components (the intraoral optics and the mouthpiece) are parts of the same portable handheld system at least during the stabilizing of method 500.

Referring to the examples set forth with respect to the previous drawings, stage 510 may be executed by mouthpiece 210, where the intraoral optics are intraoral optics 240, and the at least one bite guide is the one or more bite guides 230. Referring to the examples set forth with respect to the previous drawings, the portable handheld system may be system 200.

Stage 520 is executed during the stabilizing of stage 510, and includes capturing light directed by the intraoral optics, to provide an image of the throat which include at least part of a tonsil of the patient. Referring to the examples set forth with respect to the previous drawings, stage 520 may be executed by imaging sensor 250. It is noted that the light directed by intraoral optics may also pass through extraoral optics before being collected (e.g. by the imaging sensor), but this is not necessarily so.

Figure 19:
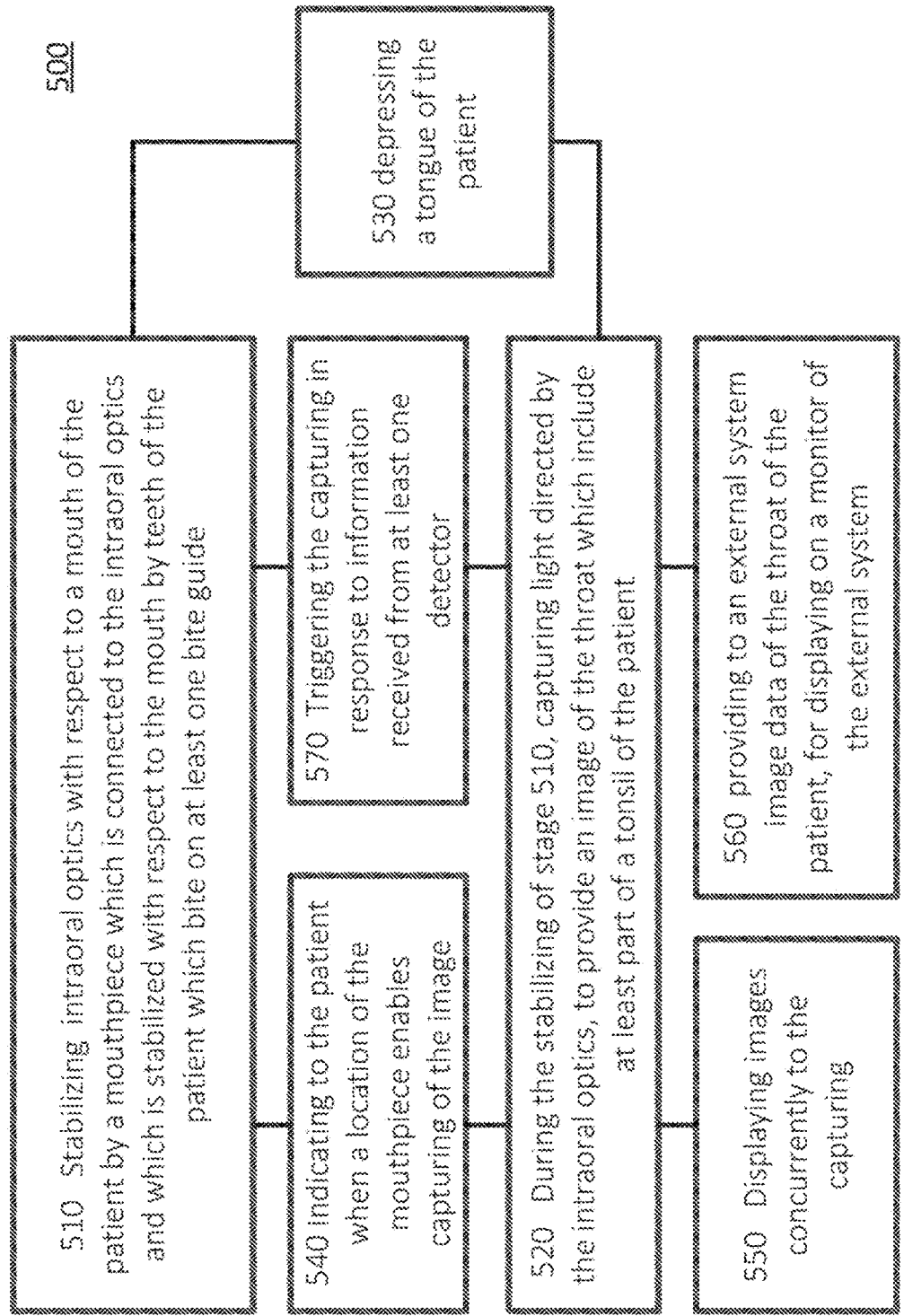
FIG. 19 is a flow chart illustrating an example of a method for imaging of a throat of a patient, in accordance with examples of the presently disclosed subject matter.

Some further examples and options of method 500 are discussed with respect to FIGS. 17, 18 and 19.

FIG. 17 illustrates optional sub-stages of the stabilizing, in accordance with examples of the presently disclosed subject matter. FIG. 18 illustrates an optional sub-stage of the capturing, in accordance with examples of the presently disclosed subject matter.

Optionally, stage 510 may include stage 511 of constraining a spatial relationship of the intraoral optics with respect to the mouthpiece so that when the patient bites on the at least one bite guide: the intraoral optics is stabilized by the mouthpiece inside a mouth of the patient having a field of view which includes at least part of a tonsil of the patient.

Optionally, stage 510 further includes stage 512 of stabilizing with respect to the mouth of the patient an imaging sensor which is mechanically connected to the mouthpiece and which executes the capturing of the image. Referring to the examples set forth with respect to the previous drawings, stage 512 may be executed by mouthpiece 210.

Optionally, stage 510 may include stage 513 of stabilizing the intraoral optics within the oral cavity proper of the patient.

Optionally, stage 510 may include stage 514 of stabilizing a posteriormost optical component of the intraoral optics posterosuperiorly to an inferiormost point of any maxillary central incisor of the patient.

Optionally, stage 520 may include stage 521 of capturing the image when a tongue of the patient is not mechanically forced down.

FIG. 19 is a flow chart illustrating an example of method 500, in accordance with examples of the presently disclosed subject matter. It is noted that method 500 may include any combination of one or more of the additional optional stages illustrated in FIG. 19 (if including any of them).

Optionally, method 500 may include stage 530 of depressing a tongue of the patient concurrently to the capturing of stage 520. Referring to the examples set forth with respect to the previous drawings, stage 530 may be executed by tongue depressor 270.

Optionally, method 500 may include stage 540 of indicating to the patient when a location of the mouthpiece enables capturing of the image. Referring to the examples set forth with respect to the previous drawings, stage 540 may be executed by a user interface of system 200 such as monitor 2020 and/or speaker 2030, e.g. based on instruction received from processor 220. It is noted that method 500 may include a stage of indicating to a user other than the patient when a location of the mouthpiece enables capturing of the image (referring to the examples set forth with respect to the previous drawings, such indicating may also be executed by a user interface of system 200 such as monitor 2020 and/or speaker 2030, e.g. based on instruction received from processor 220).

It is noted that method 500 (e.g. as part of stage 540, but not necessarily so) may include instructing the client to carry out one or more actions which are intended to clear the optical path between the lens and the tonsils (or other parts of the throat). Such actions may result in lower of the tongue by the patient. Such actions may include, for example, placing the tongue outside the mouth, uttering a specific sound, etc. The instructing may be executed by system 200, by another electronic system (e.g. a smartphone or another computer which manages the imaging process), or by another person. The instructions may be textual, verbal, and may also include playing the sound which should be uttered by the patient.

Optionally, method 500 may include optional stage 570 of triggering the capturing of the image by imaging sensor 250 stage 520 in response to information received from at least one detector of system 220. Information that would lead to triggering of image acquisition may arrive from any combination of one or more of the above identified sensors discussed with respect to system 200 (including the imaging sensor which captures the image in stage 520), and/or from other sensors.

For example, stage 570 may include of 220 may be operated to processing image date (stills or video) collected by the imaging sensor of stage 520 250 in order to recognize a selected body part (e.g. tonsil, uvula) or part thereof, and to selectively trigger capturing of the image by the imaging sensor 250 in response to results of the processing. For example, processor 220 stage 570 may include triggering the capturing of the image after it recognized that at least half of a tonsil is visible by the imaging sensor 250.

Optionally, method 500 may include stage 550 of displaying images concurrently to the capturing. Stage 550 may be executed by a display whose distance from a posteriormost bite guide out of the at least one bite guide is smaller than 10 centimeters. Referring to the examples set forth with respect to the previous drawings, stage 550 may be executed by display 2020. It is noted that the displaying may include displaying an image of the throat (in which case it is executed after stage 520), or other images (e.g. images which demonstrate that the FOV of acquisition does not include any tonsil part, in which case stage 550 may be executed before stage 520).

Method 500 may include displaying of other information on a display which is visible to the user or to another one or more people. Such other information may be displayed with or without the image. For example, method 500 may include displaying instructions indicative of a change in a state of the system which is required for enabling acquisition of the image. Such a change may be a change in location, in position, in other operational parameters, etc.

Optionally, method 500 may include stage 560 of providing to an external system image data of the throat of the patient, for displaying on a monitor of the external system. Referring to the examples set forth with respect to the previous drawings, stage 560 may be executed by communication module 5080. As discussed above with respect to system 200, this may be used for example when a display of the portable handheld system is not visible to the patient, or if such a display does not exist. It is noted that the providing may include transmitting to the external system an image of the throat including at least part of a tonsil of the patient (in which case it is executed after stage 520), or other images (e.g. images which demonstrate that the FOV of acquisition does not include any tonsil part, in which case stage 550 may be executed before stage 520).

FIG. 20 is a flow chart illustrating an example of method 600, in accordance with examples of the presently disclosed subject matter. Method 600 is a method for imaging of a throat of a patient. Referring to the examples set forth with respect to the previous drawings, method 600 may be executed by the patient, or by the patient together with another user.

Stage 610 of method 600 includes inserting partly into a mouth of the patient a mouthpiece of a portable handheld system which includes an imaging sensor which is mechanically connected to the mouthpiece. The inserting includes inserting into the mouth intraoral optics that are mechanically connected to the mouthpiece. Referring to the examples set forth with respect to the previous drawings, stage 610 may include partly into the mouth of the patient parts of system 200 (especially intraoral optics and 240 a part of mouthpiece 210). It is noted that the inserting of stage 610 may include moving and directing the portable handheld system when partially inserted in the mouth of the patient. For example, such moving and/or directing may be executed in order to direct a field of view of the portable handheld system to include one or more parts of the mouth, pharynx, etc.

It is noted that optionally, stage 610 is carried out by the patient. Optionally, stage 610 may be carried out by another user, or by a combined work of the patient and the other user.

It is noted that different degrees of insertion of the portable handheld system into the mouth may be required, e.g. based on the physical size of the portable handheld system, on the intended position within the mouth of various components of the system (e.g. the intraoral optics), on the level of comfort the patient has with inserting the system partly into her mouth, and so on. It is noted that all of the positions and configurations of the different parts of system 200 into the mouth may be the final state of the stage of inserting. All of these positions and configurations are not repeated here explicitly for reasons of brevity.

Stage 620 of method 600 includes biting by the patient on at least one bite guide of the mouthpiece, for stabilizing the mouthpiece with respect to the mouth, thereby stabilizing the intraoral optics within the mouth having a field of view which includes at least part of a tonsil of the patient.

Stage 630 of method 600 includes resuming the stabilizing at least until the imaging sensor captures an image of the throat of the patient which includes at least part of a tonsil of the patient.

After the image is acquired, method 600 may continue with opening the mouth by the patient, so as to release a holding of the portable handheld system.

After the image is acquired, method 600 may continue removing the portable handheld system from the mouth of the patient, after the patient opened the mouth for releasing the portable handheld system.

It is noted that the image captured by the imaging sensor may be later analyzed by a medical expert (e.g. a medical doctor, or another medical personnel), and the results may be provided to the patient, as well as recommendations for treatment.

Optionally, method 600 may further include optional stage 640 of receiving from a medical expert a result of a diagnosis by the medical expert which is based on the image. The receiving may include receiving the result of the diagnosis via the portable handheld system, and may also include receiving the results in other means (e.g. to another computer, in meeting, in a phone call, etc.).

Optionally, method 600 may further include optional stage 650 of receiving from a medical expert a medical recommendation for treating a medical condition of the patient, identified by the medical expert based on the image. The receiving may include receiving the medical recommendation via the portable handheld system, and may also include receiving the medical recommendation in other means (e.g. to another computer, in meeting, in a phone call, etc.). Such medical recommendations may pertain, for example, to various medical conditions which may be detected by the images obtained by the system, such as Pharyngitis, Tonsillitis, strep throat, mononucleosis, gastric reflux, and so on etc.

It is noted that moving the tongue of the patient downwards within her mouth (i.e. superiorly) may facilitate acquisition of the image which includes as much data of the tonsil as possible. Such moving down of the tongue may be achieved by depressing the tongue town mechanically, or without such a mechanical depression.

Optionally, method 600 may further include uttering by the patient a voice at least partly concurrently to the resuming, thereby lowering the tongue of the patient within the mouth for exposing the at least part of the tonsil to the intraoral optics. The uttering may be executed as part of stage 630 and/or in parallel (or partly in parallel) to stage 630. The uttering may be instructed by system 200, by another electronic system (e.g. a smartphone or another computer which manages the imaging process), or by another person. The instructions for uttering may be textual, verbal, and may also include playing the sound which should be uttered by the patient.

Reverting to the stage of inserting, it is noted that optionally, the inserting may include gripping a handgrip of the portable handheld system by the patient and moving the portable handheld system by the patient by moving the handgrip.

Optionally, the inserting may be executed by the patient in response to indications by the portable handheld system indicating when a location of the mouthpiece enables capturing of the image.

Optionally, the inserting may be executed by the user other than the patient, in response to indications by the portable handheld system indicating when a location of the mouthpiece enables capturing of the image.

Optionally, the inserting is executed by the patient (or by another user) in response to instructions by the portable handheld system indicating a change in a state of the system which is required for acquisition of the image.

Optionally, the inserting may be executed by the patient in response to image data captured by the imaging sensor which is displayed on a monitor of an external system detached from the portable handheld system. Optionally, the inserting may be executed by the user other than the patient, in response to image data captured by the imaging sensor which is displayed on a monitor of an external system detached from the portable handheld system.

It is noted that the patient may use the portable handheld system for acquiring images of other parts of her body (e.g. skin or other body orifices), at different occasions, e.g. as discussed with respect to FIG. 8. For example, method 600 may further include:
 a. detaching the mouthpiece from a casing of the portable handheld system which includes the imaging sensor;
 b. connecting to the casing a speculum for examination of a body orifice selected from the group consisting of: ear, nostril, rectum, and vagina; and
 c. holding the portable handheld system when the speculum is at least partly inserted into a respective body orifice of the patient at least until the imaging sensor captures an image of the body orifice.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

The invention claimed is:

1. A system for imaging of a body orifice of a patient, the system comprising:
 an imaging sensor operable to capture light directed thereto from within the body orifice to provide an image of the body orifice which comprises at least part of a selected body part within the body orifice of the patient;
 optics operable to collect the light from the body orifice of the patient and to direct the light towards the imaging sensor; and
 a processor configured to:

process the image of the body orifice of the patient collected by the imaging sensor in order to recognize the at least part of the selected body part within the body orifice of the patient; and selectively trigger capturing of the image by the imaging sensor in response to recognizing the at least part of the selected body part within the body orifice of the patient;

wherein the system comprises a speculum for examination of the body orifice; and wherein the imaging sensor is further operable to capture an image of the body orifice when the speculum is at least partly inserted into a respective body orifice of the patient.

2. The system according to claim 1, wherein the imaging sensor is operable to capture the image when a posteriormost optical component of the optics is located posterosuperiorly to an inferiormost point of any maxillary central incisor of the patient.

3. The system according to claim 1, further comprising a display, the display being operable to display instructions indicative of a required change in a position of the system, for enabling acquisition of the image.

4. The system according to claim 1, wherein the optics are mechanically coupled to a mouthpiece comprising at least one bite guide for stabilizing the mouthpiece with respect to teeth of the patient when the patient bites on the at least one bite guide, and wherein the mechanical coupling between the mouthpiece and the optics constrains a spatial relationship of the optics with respect to the mouthpiece so that when the patient bites on the at least one bite guide, the optics is stabilized by the mouthpiece inside a mouth of the patient having a field of view which comprises at least part of a tonsil of the patient.

5. The system according to claim 4, wherein the spatial relationship of the optics with respect to the mouthpiece as constrained by the mechanical coupling, enables the imaging sensor to image at least part of a tonsil of the patient when a tongue of the patient is not mechanically forced down.

6. The system according to claim 1, further comprising a tongue depressor mechanically coupled to a mouthpiece so as to enable the tongue depressor to depress a tongue of the patient when the patient bites on the at least one bite guide.

7. The system according to claim 1, wherein the processor is further configured and operable to provide the image to an external system operated by a medical professional in a remote location, for displaying on a monitor of the external system.

8. A method for imaging of a body orifice of a patient, the method comprising:

capturing, by an imaging sensor, light directed by optics from within the body orifice to provide an image of the body orifice which comprises at least part of a selected body part within the body orifice of the patient, wherein the imaging sensor captures the image of the body orifice when a speculum is at least partly inserted into the body orifice of the patient;

processing, by a processing resource, the image of the body orifice of the patient collected by the imaging sensor in order to recognize the at least part of the selected body part within the body orifice of the patient; and selectively triggering capturing of the image by the imaging sensor in response to recognizing the at least part of the selected body part within the body orifice of the patient, wherein the optics are part of a portable handheld system.

9. The method according to claim 8, wherein the optics are stabilized with respect to a mouth of the patient, by a mouthpiece which is coupled to the optics and which is stabilized with respect to the mouth by teeth of the patient which bite on at least one bite guide, and wherein the stabilizing further comprises stabilizing with respect to the mouth of the patient the imaging sensor which is mechanically coupled to the mouthpiece and which executes the capturing of the image.

10. The method according to claim 9, wherein the stabilizing comprises stabilizing a posteriormost optical component of the optics posterosuperiorly to an inferiormost point of any maxillary central incisor of the patient.

11. The method according to claim 8, further comprising displaying, on a display: (a) instructions indicative of a required change in a position of the portable handheld system, for enabling acquisition of the image.

12. The method according to claim 8, further comprising depressing a tongue of the patient when the patient bites on the at least one bite guide using a depressor mechanically coupled to a mouthpiece.

13. The method according to claim 8, wherein the capturing comprises capturing the image when a tongue of the patient is not mechanically forced down.

14. The method according to claim 8, further comprising providing the image to an external system operated by a medical professional in a remote location, for displaying on a monitor of the external system.

15. A non-transitory computer readable storage medium having computer readable program code embodied therewith, the computer readable program code, executable by at least one processor of a computer to perform a method comprising:

capturing, by an imaging sensor, light directed by optics from within the body orifice to provide an image of the body orifice which comprises at least part of a selected body part within the body orifice of the patient, wherein the imaging sensor captures the image of the body orifice when a speculum is at least partly inserted into the body orifice of the patient;

processing, by a processing resource, the image of the body orifice of the patient collected by the imaging sensor in order to recognize the at least part of the selected body part within the body orifice of the patient; and selectively triggering capturing of the image by the imaging sensor in response to recognizing the at least part of the selected body part within the body orifice of the patient, wherein the optics are part of a portable handheld system.

* * * * *